(12) United States Patent
Nguyen et al.

(10) Patent No.: US 7,625,924 B2
(45) Date of Patent: Dec. 1, 2009

(54) NICOTINIC ALPHA-7 RECEPTOR LIGANDS AND PREPARATION AND USES THEREOF

(75) Inventors: Truc Minh Nguyen, New York, NY (US); Wenge Xie, Mahwah, NJ (US); Richard Schumacher, Monroe, NY (US); Brian Herbert, Stockholm, NJ (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 345 days.

(21) Appl. No.: 11/312,831

(22) Filed: Dec. 21, 2005

(65) Prior Publication Data

US 2006/0167039 A1    Jul. 27, 2006

Related U.S. Application Data

(60) Provisional application No. 60/637,771, filed on Dec. 22, 2004.

(51) Int. Cl.
*A01N 43/42* (2006.01)
*A61K 31/44* (2006.01)
*C07D 513/02* (2006.01)
*C07D 515/02* (2006.01)

(52) U.S. Cl. .................. 514/301; 514/302; 514/303; 546/114; 546/115; 546/117

(58) Field of Classification Search .................. 546/114, 546/115, 117, 118, 133; 514/299, 300, 301, 514/302, 303, 305
See application file for complete search history.

(56) References Cited

U.S. PATENT DOCUMENTS

| | | | |
|---|---|---|---|
| 4,605,652 A | 8/1986 | Welstead et al. | |
| 4,775,668 A | 10/1988 | Jefson | |
| 4,789,673 A | 12/1988 | Donatsch et al. | |
| 4,798,829 A | 1/1989 | King et al. | |
| 4,845,092 A | 7/1989 | Sanger et al. | |
| 4,853,376 A * | 8/1989 | King | 514/161 |
| 4,886,808 A | 12/1989 | King | |
| 4,895,943 A | 1/1990 | Friedmann | |
| 4,910,193 A | 3/1990 | Buchheit | |
| 4,910,207 A | 3/1990 | Donatsch et al. | |
| 4,937,247 A | 6/1990 | King | |
| 4,942,160 A | 7/1990 | Sanger et al. | |
| 4,975,436 A | 12/1990 | Tyers | |
| 4,985,424 A | 1/1991 | van Wijngaarden et al. | |
| 5,017,582 A | 5/1991 | Donatsch et al. | |
| 5,034,398 A | 7/1991 | King | |
| 5,063,231 A | 11/1991 | Sanger et al. | |
| 5,098,889 A | 3/1992 | Costall et al. | |
| 5,098,909 A | 3/1992 | Williams | |
| 5,192,770 A | 3/1993 | Clark et al. | |
| 5,204,356 A | 4/1993 | Tyers | |
| 5,223,625 A | 6/1993 | van Wijngaarden et al. | |
| 5,272,154 A | 12/1993 | Dixon et al. | |
| 5,273,972 A | 12/1993 | Jagdmann et al. | |
| 5,446,050 A | 8/1995 | Rosen | |
| 5,543,426 A | 8/1996 | Dixon et al. | |
| 5,561,149 A | 10/1996 | Azria et al. | |
| 5,641,802 A | 6/1997 | Arcamone et al. | |
| 5,679,673 A | 10/1997 | Brown et al. | |
| 5,773,436 A | 6/1998 | Muller et al. | |
| 5,985,866 A | 11/1999 | Muller et al. | |
| 6,492,385 B2 | 12/2002 | Myers et al. | |
| 6,500,840 B2 | 12/2002 | Myers et al. | |
| 6,599,916 B2 | 7/2003 | Myers et al. | |
| 6,624,173 B1 | 9/2003 | Crooks et al. | |
| 6,780,861 B2 | 8/2004 | Nozulak | |
| 6,828,330 B2 | 12/2004 | Walker et al. | |
| 6,849,620 B2 | 2/2005 | Walker et al. | |
| 6,911,543 B2 | 6/2005 | Walker et al. | |
| 7,001,900 B2 | 2/2006 | Jacobsen et al. | |
| 2002/0086871 A1 | 7/2002 | O'Neill et al. | |
| 2002/0119972 A1 | 8/2002 | Leftheris et al. | |
| 2003/0073707 A1 | 4/2003 | Walker et al. | |
| 2004/0002513 A1 | 1/2004 | Mazurov et al. | |
| 2005/0182062 A1 | 8/2005 | Galli et al. | |
| 2005/0209236 A1 | 9/2005 | Luithle et al. | |
| 2005/0234095 A1 * | 10/2005 | Xie et al. | 514/305 |
| 2006/0014750 A1 | 1/2006 | O'Donnell et al. | |

FOREIGN PATENT DOCUMENTS

CA            2 361 437         3/1988

(Continued)

OTHER PUBLICATIONS

Dineley et al., the Journal of Biological Chemistry, 2002, vol. 277, pp. 22768-22780.*

(Continued)

*Primary Examiner*—D. Margaret Seaman
*Assistant Examiner*—Niloofar Rahmani
(74) *Attorney, Agent, or Firm*—Millen, White, Zelano, Branigan, P.C.

(57) ABSTRACT

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds which act as ligands for the α7 nAChR subtype, methods of preparing such compounds, compositions containing such compounds, and methods of use thereof.

34 Claims, No Drawings

FOREIGN PATENT DOCUMENTS

| | | |
|---|---|---|
| DE | 101 56 719 | 5/2003 |
| DE | 103 05 922 | 3/2004 |
| EP | 0 013 138 | 7/1980 |
| EP | 0 200 444 | 11/1986 |
| EP | 0 214 772 | 3/1987 |
| EP | 0 279 512 | 8/1988 |
| EP | 0 377 238 | 7/1990 |
| EP | 0 498 466 | 8/1992 |
| EP | 1 079 828 | 3/2001 |
| EP | 1 219 622 | 7/2002 |
| EP | 1 235 826 | 9/2002 |
| EP | 0 261 964 | 8/2008 |
| FR | 2 548 666 | 1/1985 |
| GB | 2 125 398 | 3/1984 |
| GB | 2 145 416 | 3/1985 |
| JP | 2002-30084 | 1/2002 |
| WO | WO 84/00166 | 1/1984 |
| WO | WO 85/01048 | 3/1985 |
| WO | WO 90/14347 | 11/1990 |
| WO | WO 91/09593 | 7/1991 |
| WO | WO 92/12149 | 7/1992 |
| WO | WO 93/08185 | 4/1993 |
| WO | WO 97/30998 | 8/1997 |
| WO | WO 00/45846 | 8/2000 |
| WO | WO 00/58311 | 10/2000 |
| WO | WO 01/58869 | 8/2001 |
| WO | WO 01/90109 | 11/2001 |
| WO | WO 01 92260 | 12/2001 |
| WO | WO 02/17358 | 2/2002 |
| WO | WO 02 36114 | 5/2002 |
| WO | WO 02/085901 | 10/2002 |
| WO | WO 02/096911 | 12/2002 |
| WO | WO 02/100833 | 12/2002 |
| WO | WO 02/100857 | 12/2002 |
| WO | WO 02/100858 | 12/2002 |
| WO | WO 03/022856 | 3/2003 |
| WO | WO 03 029252 | 4/2003 |
| WO | WO 03 037896 | 5/2003 |
| WO | WO 03/042210 | 5/2003 |
| WO | WO 03/051874 | 6/2003 |
| WO | WO 03/070731 | 8/2003 |
| WO | WO 03/072578 | 9/2003 |
| WO | WO 03/078431 | 9/2003 |
| WO | WO 03 080606 | 10/2003 |
| WO | WO 03/094830 | 11/2003 |
| WO | WO 03/101987 | 11/2003 |
| WO | WO 2004/014864 | 2/2004 |
| WO | WO 2004/014922 | 2/2004 |
| WO | WO 2004/016616 | 2/2004 |
| WO | WO 2004/016617 | 2/2004 |
| WO | WO 2004/029050 | 4/2004 |
| WO | WO 2004/033456 | 4/2004 |
| WO | WO 2005/001299 | 2/2005 |
| WO | WO 2005/012299 | 2/2005 |

OTHER PUBLICATIONS

S.M. Evans et al., "Probing the 5-HT$_3$ Receptor Site Using Novel Indole-3-Glyoxylic Acid Derivatives", Med. Chem. Res. (1993), 3:386-406.
Bermudez et al., J. Med. Chem. 1990. 33, 1924-1929.
D. Flammia, "Lobeline: Structure-Affinity Investigation of Nicotinic Acetylcholinergic Receptor Binding", J. Med. Chem. (1999), 42:3726-2731.
R. Azuma et al. "Metabolism and Disposition of GTS-21, A Novel Drug for Alzheimer's Disease", Xenobiotica (1999). vol. 29, No. 7, pp. 747-762.
K. E. Stevens. Et al., "Selective $\alpha_7$-nicotinic agonists normalize inhibition of auditory response in DBA mice", Psychopharmacology (1998), 136:320-327.
R. Azuma et al., "The effect of repeat administration of GTS-21 on mixed-function oxidase activities in rat", Elsevier Science Ireland Ltd., Toxicology Letters 110 (1999) pp. 137-144.
M. Decker, et al., "Neuronal Nicotinic Acetylcholine Receptors: Novel Targets for CNS Therapeutics", pp. 1-14.
M. W. Holladay et al., "Neuronal Nicotinic Acetylcholine Receptors as Targets for Drug Discovery", Journal of Medicinal Chemistry, vol. 40, No. 26, (1997), pp. 4169-4194.
Astles et al., Current Drug Targets—CNS Neurological Disorders, 2002, 1, pp. 337-348.
Mazurov et al., Biorg. & Med. Chem. Lett., 2005, No. 1 15, pp. 2073-2077.
Nurhrich et al., Eur. J. Med. Chem. 1996, No. 31, pp. 957-964.
Partial International Search Report issued May 16, 2006 in PCT/US2005/046256.
R. Tatsumi, et al., "(+)-3-[2-(Benzo[b]thiophen-2-yl)-2-oxoethyl]-1-azabicyclo[2.2.2] . . . ", Bioorganic & Medicinal Chemistry Letters, vol. 14, (2004), pp. 3781-3784.
J.E. Macor, et al., "The 5-HT$_3$ Antagonist Tropisetron (ICS 205-930) is a Potent and Selective $\alpha$7 Nicotinic Receptor Partial Agonist", Bioorganic & Medicinal Chemistry Letters, vol. 11, (2001), pp. 319-321.
International Search Report issued Aug. 11, 2006 in PCT/US2005/046256.
John E. Macor, et al. "The 5-HT$_3$ Antagonist Tropisetron (ICS 205-930) is a Potent and Selective $\alpha$7 Nicotinic Receptor Partial Agonist", Bioorganic & Medicinal Chemistry Letters 11, (2001) pp. 319-321.
Ryo Tatsumi, et al., "(+)-3-[12-(Benzo[b]thiophen-2-yl)-2-oxoethyl]-1-azabicyclo[2.2.2] . . . ", Bioorganic & Medicinal Chemistry Letters 14 (2004) pp. 3781-3784.

* cited by examiner

NICOTINIC ALPHA-7 RECEPTOR LIGANDS AND PREPARATION AND USES THEREOF

This application claims the benefit of U.S. Provisional Application Ser. No. 60/637,771, filed Dec. 22, 2004, the entire disclosure of which is hereby incorporated by reference.

FIELD OF THE INVENTION

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds, which act as ligands for the α7 nAChR subtype, methods of preparing such compounds, compositions comprising such compounds, and methods of use thereof.

BACKGROUND OF THE INVENTION

There are two types of receptors for the neurotransmitter, acetylcholine: muscarinic receptors and nicotinic receptors, based on the selectivity of action of muscarine and nicotine, respectively. Muscarinic receptors are G-protein coupled receptors. Nicotinic receptors are members of the ligand-gated ion channel family. When activated, the conductance of ions across the nicotinic ion channels increases.

Nicotinic alpha-7 receptor protein forms a homo-pentameric channel in vitro that is highly permeable to a variety of cations (e.g., $Ca^{++}$). Each nicotinic alpha-7 receptor has four transmembrane domains, named M1, M2, M3, and M4. The M2 domain has been suggested to form the wall lining the channel. Sequence alignment shows that nicotinic alpha-7 is highly conserved during evolution. The M2 domain that lines the channel is identical in protein sequence from chicken to human. For discussions of the alpha-7 receptor, see, e.g., Revah et al. (1991), *Nature,* 353, 846-849; Gatzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The nicotinic alpha-7 receptor channel is expressed in various brain regions and is believed to be involved in many important biological processes in the central nervous system (CNS), including learning and memory. Nicotinic alpha-7 receptors are localized on both presynaptic and postsynaptic terminals and have been suggested to be involved in modulating synaptic transmission. It is therefore of interest to develop novel compounds, which act as ligands for the α7 nAChR subtype, for the treatment of disease conditions associated with defective or malfunctioning nicotinic acetylcholine receptors.

SUMMARY OF THE INVENTION

This invention relates to novel compounds, which act as ligands for the α7 nAChR subtype, methods of preparing such compounds, compositions comprising such compounds, and methods of use thereof.

DETAILED DESCRIPTION OF THE INVENTION

The present invention includes compounds of Formula I:

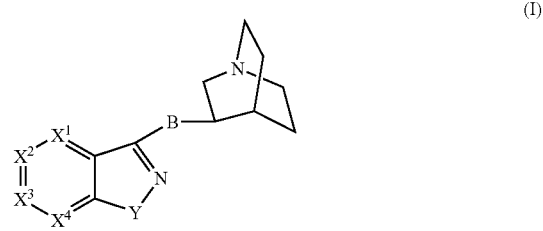

wherein
$X^1$ to $X^4$ are each, independently, N or $CR^1$, wherein at most one of $X^1$ to $X^4$ is N;
B is —C(O)—O— or —C(O)—NH—$CH_2$—;
Y is O, S, or NH;
$R^1$ is H,
  $C_{1-4}$-alkyl, or $C_{2-4}$-alkenyl, which, in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, Ar, Het, or combinations thereof (e.g., $CH_3$, $C_2H_5$, $CF_3$, $C_2H_3$, or $C_3H_5$),
  $C_{2-4}$-alkynyl which is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, $Si(C_{1-6}$-alkyl)$_3$, Ar, Het, or combinations thereof (e.g., $C_2H$, $C_3H_3$),
  $C_{1-4}$-alkoxy which is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, Ar, Het, or combinations thereof (e.g., $OCH_3$, $OC_2H_5$, $OCF_3$, $OCHF_2$),
  Ar,
  Het,
  halogen (e.g., F, Cl, Br, I),
  CN, $NO_2$, $NR^3R^4$, $SR^4$, $SOR^4$, $SO_2R^4$, $SO_2NR^3R^4$, $NR^3SO_2R^4$, $CONR^3R^4$, $CSNR^3R^4$, $COOR^4$, $NR^3COR^4$, $NR^3CSR^4$, $NR^3CONR^3R^4$, $NR^3CSNR^3R^4$, $NR^3COOR^4$, $NR^3CSOR^4$, $OCONR^3R^4$, or $OCSNR^3R^4$;
$R^2$ is H,
  $C_{1-6}$-alkyl, $C_{3-8}$-cycloalkyl, or $C_{4-8}$-cycloalkylalkyl, which, in each case, is unsubstituted or substituted one or more by F, Cl, Br, I, CN, OH, alkoxy having 1 to 4 carbon atoms, $NR^3R^4$, SH, $SR^3$, $SOR^3$, $C_{3-8}$-cycloalkyl, $SO_2R^3$, $SO_2NR^3R^4$, Ar, Het, or combinations thereof (e.g., $CH_3$, $C_2H_5$, $CF_3$, cyclopropyl, cyclobutyl, cyclopentyl, cyclopentylmethyl, cyclopropylmethyl, etc.);
$R^3$ and $R^4$ are each independently
  H,
  $C_{1-6}$-alkyl or $C_{3-6}$-alkenyl, which, in each case, is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof (e.g., $CH_3$, $C_2H_5$, $CF_3$, $C_2H_3$, or $C_3H_5$),
  $C_{3-6}$-alkynyl which is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms (e.g., diethylamino), $C_{3-8}$-cycloalkyl, $Si(C_{1-6}$-alkyl$)_3$, Ar, Het, or combinations thereof (e.g., $C_2H$, $C_3H_3$), $C_{3-8}$-cycloalkyl which is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof (e.g., cyclopropyl, cyclobutyl, cyclopentyl), $C_{4-10}$-cycloalkylalkyl which is unsubstituted or substituted in the cycloalkyl portion one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof, and/or substituted in the alkyl portion one or more times by one or more times by F, Cl, Br, 1, CN, alkoxy having 1 to 6 carbon atoms, monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof (e.g., cyclopentylmethyl, cyclopropylmethyl, etc.), Ar, or Het;

Ar is an aryl group containing 6 to 10 carbon atoms which is unsubstituted or substituted one or more times by
alkyl having 1 to 8 carbon atoms,
alkenyl having 2 to 8 carbon atoms,
alkynyl having 2 to 8 carbon atoms,
cycloalkyl having 3 to 8 carbon atoms,
cycloalkylalkyl having 4 to 10 carbon atoms,
alkoxy having 1 to 8 carbon atoms,
halogen (F, Cl, Br, or I, preferably F or Cl),
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
cycloalkylamino wherein the cycloalkyl portion has 3 to 7 carbon atoms,
cycloalkylalkylamino wherein the cycloalkylalkyl portion has 4 to 8 carbon atoms,
carboxy,
alkoxycarbonyl,
alkylaminocarbonyl,
acylamido (e.g., acetamido),
acyloxy (e.g., acetoxy),
alkylthio having 1 to 8 carbon atoms,
alkylsulphinyl having 1 to 8 carbon atoms,
alkylsulphonyl having 1 to 8 carbon atoms,
sulfo,
sulfonylamino,
aryl containing 6 to 10 carbon atoms (e.g., phenyl, naphthyl, biphenyl) which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, cyano, hydroxy, nitro, oxo or thio, heterocyclic group which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, cyano, hydroxy, nitro, oxo or thio, or combinations thereof; and Het is a heterocyclic group (e.g., furyl, thienyl, methylthienyl, bithienyl, benzylprazolyl, thiazolyl, methylthiazolyl, imidazolyl, methylimidazolyl, pyrrolidinyl, morpholinyl, thiomorpholinyl, dihydropyranyl, tetrahydropyranyl), which is fully saturated, partially saturated or fully unsaturated, having 5 to 10 ring atoms in which at least 1 ring atom is a N, O or S atom, which is unsubstituted or substituted one or more times by
alkyl having 1 to 8 carbon atoms,
alkenyl having 2 to 8 carbon atoms,
alkynyl having 2 to 8 carbon atoms,
cycloalkyl having 3 to 8 carbon atoms,
cycloalkylalkyl having 4 to 10 carbon atoms,
alkoxy having 1 to 8 carbon atoms,
halogen (F, Cl, Br, or I, preferably F or Cl),
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
cycloalkylamino wherein the cycloalkyl portion has 3 to 7 carbon atoms,
cycloalkylalkylamino wherein the cycloalkylalkyl portion has 4 to 8 carbon atoms,
carboxy,
alkoxycarbonyl,
alkylaminocarbonyl,
acylamido (e.g., acetamido),
acyloxy (e.g., acetoxy),
alkylthio having 1 to 8 carbon atoms,
alkylsulphinyl having 1 to 8 carbon atoms,
alkylsulphonyl having 1 to 8 carbon atoms,
sulfo,
sulfonylamino,
aryl containing 6 to 10 carbon atoms (e.g., phenyl, naphthyl, biphenyl) which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, cyano, hydroxy, nitro, oxo or thio, heterocyclic group which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, cyano, hydroxy, nitro, oxo or thio, or combinations thereof;

and pharmaceutically acceptable salts or solvates (e.g., hydrates) thereof, or solvates of pharmaceutically acceptable salts thereof.

According to a further aspect of the invention, the compounds of Formula I are selected from Formulas IA and IB:

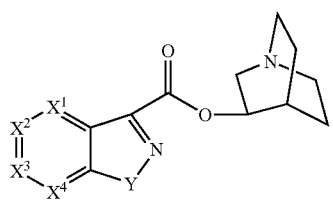

(IA)

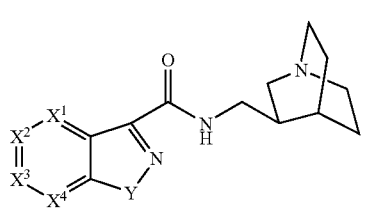

(IB)

In accordance with a further aspect of the invention, the compounds are selected from Formulas I, IA and IB wherein $R^1$ is H, $CH_3$, $C_2H_5$, $CF_3$, $C_2H_3$, or $C_3H_5$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, Ar, Het, or combinations thereof, $C_2H$ or $C_3H_3$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, $Si(C_{1-6}$-alkyl$)_3$, Ar, Het, or combinations thereof, $OCH_3$, $OC_2H_5$, $OCF_3$, or $OCHF_2$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, Ar, Het, or combinations thereof, Ar,
Het,
F, Cl, Br, I, CN, $NO_2$, $NR^3R^4$, $SR^4$, $SOR^4$, $SO_2R^4$, $SO_2NR^3R^4$, $NR^3SO_2R^4$, $CONR^3R^4$, $CSNR^3R^4$, $COOR^4$, $NR^3COR^4$, $NR^3CSR^4$, $NR^3CONR^3R^4$, $NR^3CSNR^3R^4$, $NR^3COOR^4$, $NR^3CSOR^4$, $OCONR^3R^4$, or $OCSNR^3R^4$;

$R^2$ is H,
$CH_3$, $C_2H_5$, $CF_3$, cyclopropyl, cyclobutyl, cyclopentyl, cyclopentylmethyl, or cyclopropylmethyl, which, in each case, is unsubstituted or substituted one or more by F, Cl, Br, I, CN, OH, alkoxy having 1 to 4 carbon atoms, $NR^3R^4$, SH, $SR^3$, $SOR^3$, $C_{3-8}$-cycloalkyl, $SO_2R^3$, $SO_2NR^3R^4$, Ar, Het, or combinations thereof;

$R^3$ and $R^4$ are each independently
H,
$CH_3$, $C_2H_5$, $CF_3$, $C_2H_3$, or $C_3H_5$, which, in each case, is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, $C_2H$ or $C_3H_3$, which in each case is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, $Si(C_{1-6}$-alkyl$)_3$, Ar, Het, or combinations thereof, cyclopropyl, cyclobutyl, or cyclopentyl, which in each case is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, cyclopentylmethyl or cyciopropylmethyl, which in each case is unsubstituted or substituted in the cycloalkyl portion one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, and/or substituted in the alkyl portion one or more times by one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, Ar, or
Het;

Ar is phenyl, napthyl or biphenyl, which in each case is unsubstituted or substituted one or more times by halogen, alkyl having 1 to 8 carbon atoms, hydroxy, alkoxy having 1 to 8 carbon atoms, nitro, amino, monoalkylamino having 1 to 8 carbon atoms, dialkylamino wherein the alkyl portions each have 1 to 8 carbon atoms, hydroxyalkyl having 1 to 8 carbon atoms, hydroxyalkoxy having 1 to 8 carbon atoms, carboxy, cyano, alkoxycarbonyl 2 to 9 carbon atoms, alkylthio having 1 to 8 carbon atoms, alkylsulphinyl having 1 to 8 carbon atoms, alkylsulphonyl having 1 to 8 carbon atoms, phenoxy, acetoxy, or combinations thereof; and Het is furyl, thienyl, bithienyl, benzylprazolyl, thiazolyl, imidazolyl, methylimidazolyl, pyrrolidinyl, morpholinyl, thiomorpholinyl, dihydropyranyl, or tetrahydropyranyl, which in each case is unsubstituted or substituted one or more times by halogen, alkyl having 1 to 8 carbon atoms, hydroxy, alkoxy having 1 to 8 carbon atoms, nitro, amino, monoalkylamino having 1 to 8 carbon atoms, dialkylamino wherein the alkyl portions each have 1 to 8 carbon atoms, hydroxyalkyl having 1 to 8 carbon atoms, hydroxyalkoxy having 1 to 8 carbon atoms, carboxy, cyano, alkoxycarbonyl 2 to 9 carbon atoms, alkylthio having 1 to 8 carbon atoms, alkylsulphinyl having 1 to 8 C carbon atoms, alkylsulphonyl having 1 to 8 carbon atoms, phenoxy, acetoxy, or combinations thereof, and and pharmaceutically acceptable salts or solvates (e.g., hydrates) thereof, or solvates of pharmaceutically acceptable salts thereof.

Alkyl throughout means a straight-chain or branched-chain aliphatic hydrocarbon radical having preferably 1 to 4 carbon atoms, unless otherwise indicated. Suitable alkyl groups include methyl, ethyl, propyl, isopropyl, butyl, sec-butyl, and tert-butyl. The alkyl group can also be substituted.

Alkenyl throughout means a straight-chain or branched-chain alkyl radical having preferably 2 to 6 carbon atoms, especially 2 to 4 carbon atoms, unless otherwise indicated, wherein at least one $CH_2CH_2$ group is replaced by $CH=CH$. Suitable alkenyl groups include ethenyl, propenyl, butenyl, etc. The alkenyl group can also be substituted.

Alkynyl throughout means a straight-chain or branched-chain alkyl radical having preferably 2 to 6 carbon atoms, especially 2 to 4 carbon atoms, unless otherwise indicated, wherein at least one $CH_2CH_2$ group is replaced by $C\equiv C$. Suitable alkynyl groups include ethynyl, propynyl, butynyl, etc. The alkynyl group can also be substituted.

Alkoxy means alkyl-O— groups in which the alkyl portion preferably has 1 to 4 carbon atoms, unless otherwise indicated. Suitable alkoxy groups include methoxy, ethoxy, propoxy, isopropoxy, isobutoxy, and sec-butoxy.

Cycloalkyl means a cyclic, bicyclic or tricyclic saturated hydrocarbon radical having 3 to 8 carbon atoms, unless otherwise indicated. Suitable cycloalkyl groups include cyclopropyl, cyclobutyl, cyclopentyl, and cyclohexyl. Other suitable cycloalkyl groups include spiropentyl, bicyclo[2.2.1]heptyl, and bicyclo[2.2.2]octyl.

The cycloalkyl groups can be substituted by, for example, F, Cl, Br, $C_{1-4}$-alkyl, $C_{1-4}$-alkoxy, hydroxyl, amino, monoalkylamino having 1 to 4 carbon atoms, and/or dialkyamino in which each alkyl group has 1 to 4 carbon atoms.

Cycloalkylalkyl refers to cycloalkyl-alkyl radicals in which the cycloalkyl and alkyl portions are in accordance with previous discussions. Suitable examples include cyclopropylmethyl and cyclopentylmethyl.

Cycloalkyloxy refers to cycloalkyl-oxy radicals in which the cycloalkyl portion is in accordance with previous discussions. Suitable examples include cyclopropyloxy and cyclopentyloxy.

Ar, as a group or substituent per se or as part of a group or substituent, refers to an aromatic carbocyclic radical containing 6 to 10 carbon atoms, unless indicated otherwise. Suitable aryl groups include phenyl, napthyl and biphenyl. Substituted aryl groups include the above-described aryl groups which are substituted one or more times by halogen, alkyl, hydroxy, alkoxy, nitro, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Het refers to saturated, partially saturated and fully unsaturated heterocyclic groups having one, two or three rings and a total number of 5 to 10 ring atoms wherein at least one of the ring atoms is an N, O or S atom. Preferably, the heterocyclic group contains 1 to 3 hetero-ring atoms selected from N, O and S. Suitable saturated and partially saturated heterocyclic groups include, but are not limited to tetrahydrofuranyl, tetrahydrothienyl, tetrahydropyranyl, dihydropyranyl, pyrrolidinyl, piperidinyl, piperazinyl, morpholinyl, isoxazolinyl and the like. Suitable heteroaryl groups include but are not limited to furyl, thienyl, pyrrolyl, pyrazolyl, imidazolyl, pyridyl, pyrimidinyl, indolyl, quinolinyl, isoquinolinyl, naphthyridinyl and the like. Other examples of suitable heterocyclic groups, are 2-quinolinyl, 1,3-benzodioxyl, 2-thienyl, 2-benzofuranyl, 2-benzothiophenyl, 3-thienyl, 2,3-dihydro-5-benzofuranyl, 4-indoyl, 4-pyridyl, 3-quinolinyl, 4-quinolinyl, 1,4-benzodioxan-6-yl, 3-indoyl, 2-pyrrolyl, 3,4-1,2-benzopyran-6-yl, 5-indolyl, 1,5-benzoxepin-8-yl, 3-pyridyl, 6-coumarinyl, 5-benzofuranyl, 2-isoimidazol-4-yl, 3-pyrazolyl, 3-carbazolyl, 2-thiazolyl, 2-oxazolyl, and 2-imidazolyl.

Substituted heterocyclic groups refer to the heterocyclic groups described above, which are substituted in one or more places by, for example, halogen, aryl, alkyl, hydroxy, alkoxy, cyano, trifluoromethyl, nitro, oxo, amino, alkylamino, and dialkylamino.

Radicals which are substituted one or more times preferably have 1 to 3 substituents, especially 1 or 2 substituents of the exemplified substituents. Halogenated radicals such as halogenated alkyls are preferably fluorinated and include perhalo radicals such as trifluoromethyl.

In accordance with a further aspect of the invention, $X^1$ is preferably CH.

In accordance with a further aspect of the invention, $X^2$ is CH or $CR^1$. For example, $X^2$ is CH or $CR^1$ wherein $R^1$ is Het (for example, thiazolyl, substituted thiazolyl such as alkyl substituted thiazolyl (e.g., methylthiazolyl), tetrahydropyranyl, or dihydropyranyl), $C_{1-4}$-alkoxy (for example, —$OCH_3$), or substituted $C_{1-4}$-alkoxy (e.g., —$OCF_3$ or $OCHF_2$).

In accordance with a further aspect of the invention, $X^3$ is CH or $CR^1$. For example, $X^3$ is CH or $CR^1$ wherein $R^1$ is Het (for example, thiazolyl, substituted thiazolyl such as alkyl substituted thiazolyl (e.g., methylthiazolyl), tetrahydropyranyl, or dihydropyranyl), $C_{1-4}$-alkoxy (for example, —$OCH_3$), or substituted $C_{1-4}$-alkoxy (e.g., —$OCF_3$ or $OCHF_2$).

In accordance with a further aspect of the invention, $X^4$ is CH or $CR^1$. For example, $X^4$ is CH or $CR^1$ wherein $R^1$ is substituted or unsubstituted $C_{1-4}$-alkoxy (e.g., $OCF_3$ or $OCHF_2$). More preferably, $X^4$ is CH.

In accordance with another aspect of the invention, $X^1$ to $X^4$ are each CH or $CR^1$ wherein $R^1$ is not H. According to a further aspect of the invention, $X^1$ and $X^4$ are each CH. According to a further aspect of the invention, $X^2$ is $CR^1$ wherein $R^1$ is not H, and $X^1$, $X^3$, and $X^4$ are each CH. According to a further aspect of the invention, $X^3$ is $CR^1$ wherein $R^1$ is not H, and $X^1$, $X^2$, and $X^4$ are each CH. In addition, according to a further aspect of the invention, $X^4$ $^1$S $CR^1$ wherein $R^1$ is not H, and $X^1$, $X^2$, and $X^3$ are each CH.

In accordance with a further aspect of the invention, preferred $R^1$ groups include H and Het (for example, thiazolyl, substituted thiazolyl such as alkyl substituted thiazolyl (e.g., methylthiazolyl), tetrahydropyranyl, or dihydropyranyl), $C_{1-4}$-alkoxy (for example, —$OCH_3$), or substituted $C_{1-4}$-alkoxy (e.g., —$OCF_3$ or $OCHF_2$).

In accordance with a further aspect of the invention, Y is preferably N or S, especially N.

According to a further compound and/or method aspect of the invention, the compounds of Formula I are selected from:

(3S)-1-Azabicyclo[2.2.2]oct-3-yl 5-(1,3-thiazol-2-yl)-1H-indazole-3-carboxylate, (3S)-1-Azabicyclo[2.2.2]oct-3-yl 5-(4-methyl-1,3-thiazol-2-yl)-1H-indazole-3-carboxylate 4-methylbenzenesulfonate, (3S)-1-Azabicyclo[2.2.2]oct-3-yl 5-(4-methyl-1,3-thiazol-2-yl)-1H-indazole-3-carboxylate hydroformate, (3S)-1-Azabicyclo[2.2.2]oct-3-yl 5-(4-methyl-1,3-thiazol-2-yl)-1H-indazole-3-carboxylate, (3S)-1-Azabicyclo[2.2.2]oct-3-yl 5-(5-methyl-1,3-thiazol-2-yl)-1H-indazole-3-carboxylate 4-methylbenzenesulfonate, (3)-1-Azabicyclo[2.2.2]oct-3-yl 5-(5-methyl-1,3-thiazol-2-yl)-1H-indazole-3-carboxylate hydroformate,
(3S)-1-Azabicyclo[2.2.2]oct-3-yl 5-(5-methyl-1,3-thiazol-2-yl)-1H-indazole-3-carboxylate,
(3S)-1-Azabicyclo[2.2.2]oct-3-yl 5-(difluoromethoxy)-1H-indazole-3-carboxylate hydroformate,
(3)-1-Azabicyclo[2.2.2]oct-3-yl 5-(difluoromethoxy)-1H-indazole-3-carboxylate,
(3S)-1-Azabicyclo[2.2.2]oct-3-yl 5-(tetrahydro-2H-pyran-4-yl)-1H-indazole-3-carboxylate hydroformate,
(3S)-1-Azabicyclo[2.2.2]oct-3-yl 5-(tetrahydro-2H-pyran-4-yl)-1H-indazole-3-carboxylate,
(3S)-1-Azabicyclo[2.2.2]oct-3-yl 5-(trifluoromethoxy)-1H-indazole-3-carboxylate hydroformate,
(3S)-1-Azabicyclo[2.2.2]oct-3-yl 5-(trifluoromethoxy)-1H-indazole-3-carboxylate,
(3S)-1-Azabicyclo[2.2.2]oct-3-yl 5-methoxy-1H-indazole-3-carboxylate hydroformate,
(3S)-1-Azabicyclo[2.2.2]oct-3-yl 5-methoxy-1H-indazole-3-carboxylate,
(3S)-1-Azabicyclo[2.2.2]oct-3-yl 6-(3,6-dihydro-2H-pyran-4-yl)-1H-indazole-3-carboxylate hydroformate,
(3S)-1-Azabicyclo[2.2.2]oct-3-yl 6-(3,6-dihydro-2H-pyran-4-yl)-1H-indazole-3-carboxylate,
(3S)-1-Azabicyclo[2.2.2]oct-3-yl 6-(4-methyl-1,3-thiazol-2-yl)-1H-indazole-3-carboxylate 4-methylbenzenesulfonate,
(3S)-1-Azabicyclo[2.2.2]oct-3-yl 6-(4-methyl-1,3-thiazol-2-yl)-1H-indazole-3-carboxylate,
(3S)-1-Azabicyclo[2.2.2]oct-3-yl 6-(5-methyl-1,3-thiazol-2-yl)-1H-indazole-3-carboxylate 4-methylbenzenesulfonate,
(3S)-1-Azabicyclo[2.2.2]oct-3-yl 6-(5-methyl-1,3-thiazol-2-yl)-1H-indazole-3-carboxylate hydroformate,
(3S)-1-Azabicyclo[2.2.2]oct-3-yl 6-(5-methyl-1,3-thiazol-2-yl)-1H-indazole-3-carboxylate,
(3S)-1-Azabicyclo[2.2.2]oct-3-yl 6-(tetrahydro-2H-pyran-4-yl)-1H-indazole-3-carboxylate hydroformate,
(3S)-1-Azabicyclo[2.2.2]oct-3-yl 6-(tetrahydro-2H-pyran-4-yl)-1H-indazole-3-carboxylate,
(3S)-1-Azabicyclo[2.2.2]oct-3-yl 6-(trifluoromethoxy)-1H-indazole-3-carboxylate hydroformate,
(3S)-1-Azabicyclo[2.2.2]oct-3-yl 6-(trifluoromethoxy)-1H-indazole-3-carboxylate,
(3S)-1-Azabicyclo[2.2.2]oct-3-yl 6-methoxy-1,2-benzisothiazole-3-carboxylate,
(3S)-1-Azabicyclo[2.2.2]oct-3-yl 6-methoxy-1H-indazole-3-carboxylate hydroformate,
(3S)-1-Azabicyclo[2.2.2]oct-3-yl 6-methoxy-1H-indazole-3-carboxylate,
N-1-(Azabicyclo[2.2.2]oct-3-ylmethyl)-5-trifluoromethoxy-1H-indazole-3-carboxamide hydroformate,
N-(1-Azabicyclo[2.2.2]oct-3-ylmethyl)-5-trifluoromethoxy-1H-indazole-3-carboxamide,
N-1-(Azabicyclo[2.2.2]oct-3-ylmethyl)-6-methoxy-1H-indazole-3-carboxamide hydroformate, and
N-1-(Azabicyclo[2.2.2]oct-3-ylmethyl)-6-methoxy-1H-indazole-3-carboxamide;
wherein salts listed above can also be in the form of another pharmaceutically acceptable salt, and free base forms listed above can also be in the form of a pharmaceutically acceptable salt,
wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof,) can also be in the form of a polymorph, and
wherein if the compound exhibits chirality it can be in the form of a mixture of enantiomers such as a racemate or a mixture of diastereomers, or can be in the form of a single enantiomer or a single diastereomer.

According to a further compound and/or method aspect of the invention, the compounds of Formula I are selected from:
1-Azabicyclo[2.2.2]oct-3-yl 5-methoxy-1H-indazole-3-carboxylate hydroformate,
1-Azabicyclo[2.2.2]oct-3-yl 5-methoxy-1H-indazole-3-carboxylate,
(3S)-1-Azabicyclo[2.2.2]oct-3-yl 6-ethoxy-1,2-benzisothiazole-3-carboxylate hydroformate,
(3S)-1-Azabicyclo[2.2.2]oct-3-yl 6-ethoxy-1,2-benzisothiazole-3-carboxylate,
(3R)-1-Azabicyclo[2.2.2]oct-3-yl 5-methoxy-1H-indazole-3-carboxylate hydroformate,
(3R)-1-Azabicyclo[2.2.2]oct-3-yl 5-methoxy-1H-indazole-3-carboxylate,
(3R)-1-Azabicyclo[2.2.2]oct-3-yl 6-methoxy-1H-indazole-3-carboxylate hydroformate,
(3R)-1-Azabicyclo[2.2.2]oct-3-yl 6-methoxy-1H-indazole-3-carboxylate,
(3R)-1-Azabicyclo[2.2.2]oct-3-yl 7-methoxy-1H-indazole-3-carboxylate hydroformate,
(3R)-1-Azabicyclo[2.2.2]oct-3-yl 7-methoxy-1H-indazole-3-carboxylate,
(3R)-1-Azabicyclo[2.2.2]oct-3-yl 6-(difluoromethoxy)-1H-indazole-3-carboxylate hydroformate,
(3R)-1-Azabicyclo[2.2.2]oct-3-yl 6-(difluoromethoxy)-1H-indazole-3-carboxylate,
(3R)-1-Azabicyclo[2.2.2]oct-3-yl 5-(trifluoromethoxy)-1H-indazole-3-carboxylate,
(3R)-1-Azabicyclo[2.2.2]oct-3-yl 6-(trifluoromethoxy)-1H-indazole-3-carboxylate hydroformate,
(3R)-1-Azabicyclo[2.2.2]oct-3-yl 6-(trifluoromethoxy)-1H-indazole-3-carboxylate,
(3R)-1-Azabicyclo[2.2.2]oct-3-yl 7-(trifluoromethoxy)-1H-indazole-3-carboxylate hydroformate,
(3R)-1-Azabicyclo[2.2.2]oct-3-yl 7-(trifluoromethoxy)-1H-indazole-3-carboxylate,
(3R)-1-Azabicyclo[2.2.2]oct-3-yl 5-(4-methyl-1,3-thiazol-2-yl)-1H-indazole-3-carboxylate hydroformate,
(3R)-1-Azabicyclo[2.2.2]oct-3-yl 5-(4-methyl-1,3-thiazol-2-yl)-1H-indazole-3-carboxylate,
(3R)-1-Azabicyclo[2.2.2]oct-3-yl 5-(5-methyl-1,3-thiazol-2-yl)-1H-indazole-3-carboxylate hydroformate,
(3R)-1-Azabicyclo[2.2.2]oct-3-yl 5-(5-methyl-1,3-thiazol-2-yl)-1H-indazole-3-carboxylate,
(3R)-1-Azabicyclo[2.2.2]oct-3-yl 6-(4-methyl-1,3-thiazol-2-yl)-1H-indazole-3-carboxylate hydroformate,
(3R)-1-Azabicyclo[2.2.2]oct-3-yl 6-(4-methyl-1,3-thiazol-2-yl)-1H-indazole-3-carboxylate,
(3R)-1-Azabicyclo[2.2.2]oct-3-yl 6-(5-methyl-1,3-thiazol-2-yl)-1H-indazole-3-carboxylate hydroformate,
(3R)-1-Azabicyclo[2.2.2]oct-3-yl 6-(5-methyl-1,3-thiazol-2-yl)-1H-indazole-3-carboxylate,
(3R)-1-Azabicyclo[2.2.2]oct-3-yl 5-(3,6-dihydro-2H-pyran-4-yl)-1H-indazole-3-carboxylate hydroformate, and
(3R)-1-Azabicyclo[2.2.2]oct-3-yl 5-(3,6-dihydro-2H-pyran-4-yl)-1H-indazole-3-carboxylate, wherein salts listed above can also be in the form of another pharmaceutically acceptable salt, and free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

Preferred aspects include pharmaceutical compositions comprising a compound of this invention and a pharmaceutically acceptable carrier and, optionally, another active agent as discussed below; a method of stimulating or activating inhibiting alpha-7 nicotinic receptors, e.g., as determined by a conventional assay or one described herein, either in vitro or in vivo (in an animal, e.g., in an animal model, or in a mammal or in a human); a method of treating a neurological syndrome, e.g., loss of memory, especially long-term memory, cognitive impairment or decline, memory impairment, etc. method of treating a disease state modulated by nicotinic alpha-7 activity, in a mammal, e.g., a human, e.g., those mentioned herein.

The compounds of the present invention may be prepared conventionally. Some of the known processes that can be used are described below. All starting materials are known or can be conventionally prepared from known starting materials.

The synthesis of similar compounds is disclosed in copending U.S. application Ser. No. 10/669,645, filed Sep. 25, 2003, and Ser. No. 11/089,533, filed Mar. 25, 2005, the entire disclosures of which are hereby incorporated by reference.

Acids that can be used in the preparation of the bicyclobase esters are commercially available, can be prepared by known procedures described in the literature, or as described below. For example, 7-trifluoromethoxyindazole-3-carboxylic acid is commercially available. 5-Nitroindazole-3-acid can be prepared by nitration of indazole-3-acid (Kamm, O.; Segur, J. B. *Org. Syn. Coll.* Vol 1. 1941, 372). Bromoindazole acids and 5-trifluoromethoxyindazole-3-acid can be prepared from the corresponding isatins by basic hydrolysis, diazotization, and reduction (Snyder, H. R.; et al. *J. Am. Chem. Soc.* 1952, 74, 2009). 3-Substituted benzisothiazolecarboxylic acids can be prepared from the corresponding thiophenols by reaction with oxalyl chloride and aluminum chloride followed by treatment with hydroxylamine, hydrogen peroxide, and sodium hydroxide. The thiazole substituted indazole acids can be prepared from the bromoindazole acids by esterification, palladium mediated cross-coupling with the requisite thiazole zinc reagent (Reeder, M. R.; et. al. *Org. Proc. Res. Devel.* 2003, 7, 696), and saponification. The oxazole substituted indazole acids were prepared in a similar manner. The dihydropyran and tetrahydropyran substituted indazole acids can be prepared from the bromo acids by esterification, metal-halogen exchange and trapping with tetrahydropyran-4-one, followed by acid-mediated dehydration or reduction under acidic conditions. Some substituted indazole-3-acids were prepared from simple benzene derivatives. For example, 5-difluoromethoxyindazole-3-acid was prepared from 3-bromo-4-nitrophenol by reaction with ethyl difluoroacetate, reaction with diethyl malonate, decarboxylative saponification, esterification, reduction of the nitro group, and diazotization. 6-Difluoromethoxyindazole-3-acid was prepared in a similar manner from 2-bromo-5-difluoromethoxynitrobenzene. The 2-bromo-5-difluoromethoxynitrobenzene used in that preparation was prepared from 4-nitrophenol by ether formation, nitro reduction with concomitant protection as the amide, nitration, amide hydrolysis, and a Sandmeyer reaction with copper (I) bromide. The bicycloamine used to prepare the amide derivatives was readily prepared from quinuclidinone by reaction with tosylmethylisocyanide followed by reduction.

The bicyclobase esters can be prepared by the coupling reaction of acids with the bicycloalcohol using triphenylphosphine and diisopropyl azodicarboxylate. (Ahn, C.; Correia, R.; DeShong, P. *J. Org. Chem.,* 2002, 67, 1751). Alternatively, the bicyclobase esters can be prepared by the reaction of the acids with the bicycloalcohol in the presence of either p-toluenesulfonyl chloride or oxalyl chloride in pyridine. (Brewster, J. H.; Ciotti Jr., C. J. *J. Am. Chem. Soc.,* 1955, 77, 6214). The bicyclobase amides can be prepared by the coupling reaction of acids with the bicycloamine and HBTU, HATU, or HOBt and EDCI in DMF, or by converting the acids to the corresponding acid chloride and then reaction with the bicycloamine (Macor, J. E.; Gurley, D.; Lanthorn, T.; Loch, J.; Mack, R. A.; Mullen, G.; Tran, O.; Wright, N.; Macor, J. E. *Bioog. Med. Chem. Lett.* 2001, 9, 319-321). The couplings are generally performed at 0° C. and maintained at room temperature for 18-24 hours. The resultant adducts can be isolated and purified by standard techniques, such as chromatography or recrystallization, practiced by those skilled in the art.

One of ordinary skill in the art will recognize that compounds of Formulas I, IA, and IB can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulas I, IA, and IB can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a bas with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, a maleate, or an alkyllbenzenesulfonate salt (e.g., a $C_{1-4}$-alkyllbenzenesulfonate salt such as 4-methylbenzenesulfonate salt).

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of Formulas I, IA, and IB can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of Formulas I, IA, and IB can exist in different solvate forms. Solvates of the compounds of the invention may also form when solvent molecules are incorporated into the crystalline lattice structure of the compound molecule during the crystallization process.

The compounds of the invention can be administered alone or as an active ingredient of a formulation. Thus, the present invention also includes pharmaceutical compositions of compounds of Formulas I, IA, or IB, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their alpha-7 stimulating activity and, preferably their high degree of selectivity, the compounds of the present invention can be administered to anyone needing stimulation of alpha-7 receptors. Administration may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or memory loss, e.g., other α-7 agonists, PDE4 inhibitors, calcium channel blockers, muscarinic m1 and m2 modulators, adenosine receptor modulators, ampakines NMDA-R modulators, mGluR modulators, dopamine modulators, serotonin modulators, cannabinoid modulators, and cholinesterase inhibitors (e.g., donepezil, rivastigimin and glanthanamine). In such combinations, each active ingredient can be administered either in accordance with their usual dosage range or a dose below their usual dosage range.

The compounds of the invention can be used in conjunction with "positive modulators" which enhance the efficacy of nicotinic receptor agonists. See, e.g., the positive modulators disclosed in WO 99/56745, WO 01/32619, and WO 01/32622. Such combinational therapy can be used in treating conditions/diseases associated with reduced nicotinic transmission.

Further the compounds may be used in conjunction with compounds that bind to Aβ peptides and thereby inhibit the binding of the peptides to α7nAChr subtypes. See, e.g., WO 99/62505.

The compounds of the present invention are nicotinic alpha-7 ligands, preferably agonists, especially partial agonists, for the alpha-7 nicotinic acetylcholine receptor. Assays for determining nicotinic acetylcholine activity are known within the art. See, e.g., Davies, A. R., et al., *Characterisation of the binding of [3H]methyllycaconitine: a new radioligand for labelling alpha 7-type neuronal nicotinic acetylcholine receptors*. Neuropharmacology, 1999. 38(5): p. 679-90. As agonists for α-7 nAChRs, the compounds are useful in the prophylaxis and treatment of a variety of diseases and conditions associated with the central nervous system. Nicotinic acetylcholine receptors are ligand-gastrol ion-channel receptors that are composed of five subunit proteins which form a central ion-conducting pore. Presently, there are eleven known neuronal nAChR subunits (α2-α9 and β2-β4). There are also five further subunits expressed in the peripheral nervous system (α1, β1, γ, δ, ε).

The nAChR receptor subtypes can be homopentameric or heteropentameric. The subtype which has received considerable attention is the homopentameric α7 receptor subtype formed from five α7 subunits. The α7nAChRs exhibit a high affinity for nicotine (agonist) and for α-bungarotoxin (antagonist). Studies have shown the α7-nAChR agonists can be useful in the treatment of psychotic diseases, neurodegenerative diseases, and cognitive impairments, among other things.

While nicotine is a known α7 agonist, there is a need for the development of other α7-nAChR agonists, especially selective agonists, that are less toxic or exhibit fewer side effects than nicotine.

The compound anabaseine, i.e., 2-(3-pyridyl)-3,4,5,6-tetrahydropyridine is a naturally occurring toxin in certain marine worms (nemertine worms) and ants. See, e.g., Kem et al., Toxicon, 9:23, 1971. Anabaseine is a potent activator of mammalian nicotinic receptors. Se e.g., Kem, Amer. Zoologist, 25, 99, 1985. Certain anabaseine analogs such as anabasine and DMAB (3-[4-(dimethylamino)benzylidene]-3,4, 5,6-tetrahydro-2',3'-bipyridine) are also known nicotinic receptor agonists. See, e.g., U.S. Pat. No. 5,602,257 and WO 92/15306. One particular anabaseine analog, (E-3-[2,4-dimethoxy-benzylidene]-anabeseine, also known as GTS-21 and DMXB (se e.g., U.S. Pat. No. 5,741,802), is a selective partial α7-nAChR agonist that has been studied extensively. For example, abnormal sensory inhibition is a sensory processing deficit in schizophrenics and GTS-21 has been found to increase sensory inhibition through interaction with α7-nAChRs. See, e.g., Stevens et al., Psychopharmacology, 136: 320-27 (1998).

Another compound which is known to be a selective α7-nAChR agonist is Tropisetron, i.e., 1αH, 5αH-tropan-3α-yl indole-3-carboxylate. See J. E. Macor et al., *The 5-HT3-Antagonist Tropisetron (ICS 205-930) is a Potent and Selective A7 Nicotinic Receptor Partial Agonist*. Bioorg. Med. Chem. Lett. 2001, 319-321).

The present invention further includes methods of treatment that involve activation of α-7 nicotinic receptors. Thus, the present invention includes methods of selectively activating/stimulating α-7 nicotinic receptors in animals, e.g., mammals, especially humans, wherein such activation/stimulation has a therapeutic effect, such as where such activation may relieve conditions involving neurological syndromes, such as the loss of memory, especially long-term memory. Such methods comprise administering to an animal in need thereof, especially a mammal, most especially a human, an effective amount of a compound of Formulas I, IA, or IB, alone or as part of a formulation, as disclosed herein.

In accordance with a method aspect of the invention, there is provided a method of treating a patient (e.g., a mammal such as a human) suffering from a disease state (e.g., memory impairment) comprising administering to the patient a compound according to Formulas I, IA, or IB. Preferably, the disease state involves decreased nicotinic acetylcholine receptor activity.

In accordance with a method aspect of the invention there is provided a method for the treatment or prophylaxis of a disease or condition resulting from dysfunction of nicotinic acetylcholine receptor transmission in a mammal, e.g. a human, comprising administering an effective amount of a compound according to Formulas I, IA, or IB.

In accordance with a method aspect of the invention there is provided a method for the treatment or prophylaxis of a disease or condition resulting from defective or malfunctioning nicotinic acetylcholine receptors, particularly α7nACh receptors, in a mammal, e.g. a human, comprising administering an effective amount of a compound according to Formulas I, IA, or IB.

In accordance with a method aspect of the invention there is provided a method for the treatment or prophylaxis of a disease or condition resulting from suppressed nicotinic acetylcholine receptor transmission in a mammal, e.g., a human, comprising administering an amount of a compound according to Formulas I, IA, or IB effective to activate α7nACh receptors.

In accordance with another method aspect of the invention there is provided a method for the treatment or prophylaxis of a psychotic disorder, a cognition impairment (e.g., memory impairment), or neurodegenerative disease in a mammal, e.g., a human, comprising administering an effective amount of a compound according to Formulas I, IA, or IB.

In accordance with another method aspect of the invention there is provided a method for the treatment or prophylaxis of a disease or condition resulting from loss of cholinergic synapses in a mammal, e.g., a human, comprising administering an effective amount of a compound according to Formulas I, IA, or IB.

In accordance with another method aspect of the invention there is provided a method for the treatment or prophylaxis of a neurodegenerative disorder by activation of α7nACh receptors in a mammal, e.g., a human, comprising administering an effective amount of a compound according to Formulas I, IA, or IB.

In accordance with another method aspect of the invention there is provided a method for protecting neurons in a mammal, e.g., a human, from neurotoxicity induced by activation of α7nACh receptors comprising administering an effective amount of a compound according to Formulas I, IA, or IB.

In accordance with another method aspect of the invention there is provided a method for the treatment or prophylaxis of a neurodegenerative disorder by inhibiting the binding of Aβ peptides to α7nAC receptors in a mammal, e.g., a human, comprising administering an effective amount of a compound according to Formulas I, IA, or IB.

In accordance with another method aspect of the invention there is provided a method for protecting neurons in a mammal, e.g., a human, from neurotoxicity induced by Aβ peptides comprising administering an effective amount of a compound according to Formulas I, IA, or IB.

In accordance with another method aspect of the invention there is provided a method for alleviating inhibition of cholinergic function induced by Aβ peptides in a mammal, e.g., a human, comprising administering an effective amount of a compound according to Formulas I, IA, or IB.

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, treating jetlag, treating nflammation, and treating sepsis. See, e.g., WO 97/30998; WO 99/03850; WO 00/42044; WO 01/36417; Holladay et al., J. Med. Chem., 40:26, 4169-94 (1997); Schmitt et al., Annual Reports Med. Chem., Chapter 5, 41-51 (2000); Stevens et al., Psychopharmatology, (1998) 136: 320-27 (1998); and Shytle et al., Molecular Psychiatry, (2002), 7, pp. 525-535.

Thus, in accordance with the invention, there is provided a method of treating a patient, especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound according to Formulas I, IA, or IB.

Neurodegenerative disorders included within the methods of the present invention include, but are not limited to, treatment and/or prophylaxis of Alzheimer's diseases, Pick's disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Straussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, α-7nAChRs agonists, such as the compounds of the present invention can be used to treat age-related dementia and other dementias and conditions with memory loss including age-related memory loss, senility, vascular dementia, diffuse white matter disease (Binswariger's disease), dementia of endocrine or metabolic origin, dementia of head trauma and diffuse brain damage, dementia pugilistica and frontal lobe dementia. See, e.g., WO 99/62505. Thus, in accordance with the invention, there is provided a method of treating a patient, especially a human, suffering from age-related dementia and other dementias and conditions with memory loss comprising administering to the patient an effective amount of a compound according to Formulas I, IA, or IB.

Thus, in accordance with a further embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formulas I, IA, or IB.

Amyloid precursor protein (APP) and Aβ peptides derived therefrom, e.g., $A\beta_{1-40}$, $A\beta_{1-42}$, and other fragments, are known to be involved in the pathology of Alzheimer's disease. The $A\beta_{1-42}$ peptides are not only implicated in neurotoxicity but also are known to inhibit cholinergic transmitter function. Further, it has been determined that Aβ peptides bind to α-7 nAChRs. Thus, agents which block the binding of the Aβ peptides to α-7 nAChRs are useful for treating neurodegenerative diseases. See, e.g., WO 99/62505. In addition, stimulation α-7 nAChRs can protect neurons against cytotoxicity associated with Aβ peptides. See, e.g., Kihara, T. et al., Ann. Neurol., 1997, 42, 159.

Thus, in accordance with an embodiment of the invention there is provided a method of treating and/or preventing dementia in an Alzheimer's patient which comprises administering to the subject a therapeutically effective amount of a compound according to Formulas I, IA, or IB to inhibit the binding of an amyloid beta peptide (preferably, $A\beta_{1-42}$) with nAChRs, preferable α-7 nAChRs, most preferably, human α-7 nAChRs (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The present invention also provides methods for treating other amyloidosis diseases, for example, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

In addition, nicotinic receptors have been implicated as playing a role in the body's response to alcohol ingestion. Thus, agonists for α-7nAChR's can be used in the treatment of alcohol withdrawal and in anti-intoxication therapy. Thus, in accordance with an embodiment of the invention there is provided a method of treating a patient for alcohol withdrawal or treating a patient with anti-intoxication therapy comprising administering to the patient an effective amount of a compound according to Formulas I, IA, or IB.

Agonists for the α-7nAChR subtypes can also be used for neuroprotection against damage associated with strokes and ischemia and glutamate-induced excitotoxicity. Thus, in accordance with an embodiment of the invention there is provided a method of treating a patient to provide for neuroprotection against damage associated with strokes and ischemia and glutamate-induced excitotoxicity comprising administering to the patient an effective amount of a compound according to Formulas I, IA, or IB.

As noted above, agonists for the α-7nAChR subtypes can also be used in the treatment of nicotine addiction, inducing smoking cessation, treating pain, and treating jetlag, obesity, diabetes, inflammation, and sepsis. Thus, in accordance with an embodiment of the invention there is provided a method of treating a patient suffering from nicotine addiction, pain, jetlag, obesity and/or diabetes, or a method of inducing smoking cessation in a patient comprising administering to the patient an effective amount of a compound according to Formulas I, IA, or IB.

The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. Therefore, compounds with affinity for the α7nACh receptor on macrophages may be useful for human inflammatory diseases including rheumatoid arthritis, diabetes and sepsis. See, e.g., Czura, C J et al, J. Intern. Med., 2005, 257(2), 156-66.

Thus, in accordance with an embodiment of the invention there is provided a method of treating a patient (e.g., a mammal, such as a human) suffering from an inflammatory disease, such as, but not limited to, rheumatoid arthritis, diabetes or sepsis, comprising administering to the patient an effective amount of a compound according to Formulas I, IA, or IB.

In addition, due to their affinity to α-7nAChR's, labeled derivatives of the compounds of Formulas I, IA, or IB (e.g., $C^{11}$ or $F^{18}$ labelled derivatives), can be used in neuroimaging of the receptors within, e.g., the brain. Thus, using such labeled agents in vivo imaging of the receptors can be performed using, e.g., PET imaging.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeldt-Jakob disease, HIV, cardiovascular disease, and head trauma as well as age-related cognitive decline.

Thus, in accordance with an embodiment of the invention there is provided a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (e.g., dogs, cats, horses, etc.) patient comprising administering to the patient an effective amount of a compound according to Formulas I, IA, or IB.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention can be administered to mammals, particularly humans, at typical dosage levels customary for α-7 nicotinic receptor agonists such as the known α-7 nicotinic receptor agonist compounds mentioned above. For example, the compounds can be administered, in single or multiple doses, by oral administration at a dosage level of, for example, 0.0001-10 mg/kg/day, e.g., 0.01-10 mg/kg/day. Unit dosage forms can contain, for example, 1-200 mg of active compound. For intravenous administration, the compounds can be administered, in single or multiple dosages.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results.

Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

EXAMPLES

All spectra were recorded at 300 MHz on a Bruker Instruments NMR unless otherwise stated. Coupling constants (J) are in Hertz (Hz) and peaks are listed relative to TMS ($\delta$ 0.00 ppm). Microwave reactions were performed using a Personal Chemistry Optimizer™ microwave reactor in 2.5 mL or 5 mL Personal Chemistry microwave reactor vials. All reactions were performed at 200° C. for 600 s with the fixed hold time ON unless otherwise stated. Sulfonic acid ion exchange resins (SCX) were purchased from Varian Technologies. Analytical HPLC was performed on 4.6 mm×100 mm Xterra $RP_{18}$ 3.5μ columns using a gradient of 20/80 to 80/20 water (0.1% formic acid)/acetonitrile (0.1% formic acid) over 6 min. Preparative HPLC was performed on 30 mm×100 mm Xtera Prep $RP_{18}$ 5μ columns using an 8 min gradient of 95/5 to 20/80 water (0.1% formic acid)/acetonitrile (0.1% formic acid).

Representative Procedures.

I. Acid Syntheses

Procedure 1

Procedure 1 provides a method for the conversion of substituted isatins to the corresponding indazole-3-carboxylic acids.

The conversion of the substituted isatins to the corresponding indazole-3-carboxylic acids is essentially the same method as described for indazole-3-carboxylic acid: Snyder, H. R., et. al. *J. Am. Chem. Soc.* 1952, 74, 2009. The substituted isatin (22.1 mmol) was diluted with 1 N sodium hydroxide (24 mL) and was heated at 50° C. for 30 min. The burgundy solution was allowed to cool to rt and was maintained for 1 h. The reaction mixture was cooled to 0° C. and was treated with a 0° C. solution of sodium nitrite (22.0 mmol) in water (5.5 mL). This solution was added through a pipet submerged below the surface of a vigorously stirred solution of sulfuric acid (2.3 mL) in water (45 mL) at 0° C. The addition took 15 min and the reaction was maintained for an additional 30 min. A cold (0° C.) solution of tin (II) chloride dihydrate (52.7 mmol) in concentrated hydrochloric acid (20 mL) was added to the reaction mixture over 10 min and the slurry was maintained for 60 min. The precipitated solids were isolated by filtration, washed with water, and dried to give a quantitative mass balance. The solid was recrystallized from acetic acid (20 mL/g) to provide the acid as a light yellow solid. The acids were coupled with 1,4-diazabicyclo[3.2.2]nonane according to procedure A.

The following acids were prepared according to this method:
5-Bromo-1H-indazole-3-carboxylic acid,
5-Methoxy-1H-indazole-3-carboxylic acid,
6-Methoxy-1H-indazole-3-carboxylic acid,
7-Methoxy-1H-indazole-3-carboxylic acid,
5-(Trifluoromethoxy)-1H-indazole-3-carboxylic acid, and
6-(Trifluoromethoxy)-1H-indazole-3-carboxylic acid.

Procedure 2

Procedure 2 provides a method for the preparation of 5-difluoromethoxyindazole-3-acid from 3-bromo-4-nitrophenol.

3-Bromo-4-nitrophenol (10.0 mmol) was added to a suspension of sodium hydroxide (29.0 mmol) in N,N-dimethylformamide (15 mL) and the suspension was maintained for 15 min at rt. The reaction mixture was cooled to 0° C. and was treated with ethyl chlorodifluoroacetate (20.0 mmol). The reaction mixture was heated at 70° C. for 16 h and was concentrated. The residue was diluted with ice water (200 mL) and was extracted with ethyl acetate (3×100 mL). The combined organic layers were dried (magnesium sulfate) and concentrated to provide the difluoromethyl ether in 75% yield as a yellow oil.

Diethyl malonate (328 mmol) was added dropwise to a suspension of sodium hydride (328 mmol) in dimethylsulfoxide (40 mL) at 0° C. The reaction mixture was warmed to 60° C. and maintained for 0.5 h. A solution of the difluoromethyl ether (149 mmol) in dimethylsulfoxide (80 mL) was added dropwise and the reaction mixture was heated at 100° C. for 5 h. The cooled solution was poured onto ice water, and the aqueous layer was extracted with dichloromethane (3×100 mL). The combined organic layers were dried (magnesium sulfate) and concentrated to give the crude diester in 112% yield as an oil. The diester (167 mmol), sodium hydroxide (500 mmol), and water (335 mL) were combined and heated at 60° C. for 1 h. The reaction mixture was allowed to cool to rt and the aqueous layer was washed with dichloromethane (3×100 mL). The pH of the aqueous layer was cautiously adjusted to 1 with concentrated hydrochloric acid and the reaction mixture was heated at 60° C. for 1 h. The suspension was cooled to 5° C. and the solids were collected by filtration and dried to provide the acid in 61% yield.

Acetyl chloride (203 mmol) was added dropwise to ethanol (300 mL) at 0° C. After 0.5 h, the acid (101 mmol) was added and the reaction mixture was heated at reflux for 15 h. The reaction mixture was concentrated and the residue was partitioned between dichloromethane (200 mL) and saturated sodium bicarbonate (100 mL). The aqueous layer was further extracted with dichloromethane (2×200 mL) and the combined organic layers were dried (magnesium sulfate) and concentrated to provide the ester in 60% yield as a brown oil.

The ester (60.4 mmol) was dissolved in ethanol (103 mL), diluted with water (71 mL), and was treated with ammonium chloride (243 mmol) and iron powder (301 mmol). The reaction mixture was heated at reflux for 10 minutes and the suspension was filtrated through Celite and the filter cake was washed with ethanol three times. The filtrate was concentrated, the residue was suspended in 2 N hydrochloric acid and was stirred vigorously for 0.5 h. The aqueous layer was washed with ethyl acetate (3×50 mL) and the pH adjusted to 9-10 with 5 M sodium hydroxide. The aqueous layer was extracted with chloroform (3×100 mL) and the combined organic layers were dried (magnesium sulfate). Acetic anhydride (392 mmol), isoamyl nitrite (291 mmol), and potassium acetate (51.0 mmol) were added to the organic layer and the suspension was heated at reflux for 16 h. The solution was evaporated and the residue was partitioned between saturated sodium bicarbonate (50 mL) and dichloromethane (100 mL). The aqueous layer was further extracted with dichloromethane (2×100 mL) and the combined organic layers were dried (magnesium sulfate) and concentrated to provide the N-acetylindazole ester in 79% yield as a brown oil.

The ester (63.8 mmol), sodium hydroxide (193 mmol), and water (65 mL) were combined and the reaction was maintained for 24 h at 60° C. After cooling to rt, the aqueous layer was washed with dichloromethane (3×50 mL). The aqueous layer was adjusted to pH 1 with concentrated hydrochloric acid. The precipitated solids were collected by filtration, washed with water and dichloromethane, and dried to provide the acid in 27% yield.

The following acids were prepared according to this method:

5-(Difluoromethoxy)-1H-indazole-3-carboxylic acid.

Procedure 3

Procedure 3 provides a method for the coupling between the brominated carboxylic esters and zinc reagents to form alkyl- and aryl-substituted derivatives.

A 5 mL microwave reaction vessel was charged with bis(triphenylphosphine)palladium (II) chloride (0.030 mmol, 0.1 eq) and the bromo ester (0.30 mmol). The vessel was evacuated and back-filled with argon gas. In a separate reaction vessel, solution of the Grignard (1.2 mmol, 4 eq) was added to a 0.5 M solution of zinc chloride (1.2 mmol, 4 eq) in tetrahydrofuran at rt. The suspension was maintained for 30 min and the entire contents were transferred to the reaction vessel via cannula. The vessel was sealed and subjected to microwave irradiation at 100° C. for 600 sec. The reaction was quenched with acetic acid (0.5 mL) and concentrated. The residue was diluted with saturated sodium bicarbonate and extracted with 9/1 dichloromethane/methanol (5×40 mL). The combined organic layers were dried (sodium sulfate) and concentrated. The residue was purified by chromatography (1/1 to 0/1 hexane/ethyl acetate) to provide the ester. The ester was added to a solution of 2 N sodium hydroxide and the suspension was warmed to 60° C. After 2 h the solution was allowed to cool to room temperature and was acidified to pH~2. The precipitated solids were collected by filtration, washed with water, and dried to provide the acid as an off-white to light yellow solid. The acid was coupled with 1,4-diazabicyclo[3.2.2]nonane according to procedure A.

The Grignard reagent of thiazole is commercially available. Alternatively, the aryllithium and the corresponding arylzinc reagent can be generated according to the procedure outlined by Reeder, M. R.; et. al. *Org. Proc. Res. Devel.* 2003, 7, 696. The zinc reagents of oxazole, and related reagents were prepared according to this procedure.

The following acids were prepared according to this method:

5-(1,3-Thiazol-2-yl)-1H-indazole-3-carboxylic acid,
6-(1,3-Thiazol-2-yl)-1H-indazole-3-carboxylic acid,
6-(1,3-Oxazol-2-yl)-1H-indazole-3-carboxylic acid,
5-(4-Methyl-1,3-thiazol-2-yl)-1H-indazole-3-carboxylic acid,
5-(5-Methyl-1,3-thiazol-2-yl)-1H-indazole-3-carboxylic acid,
6-(4-Methyl-1,3-thiazol-2-yl)-1H-indazole-3-carboxylic acid, and
6-(5-Methyl-1,3-thiazol-2-yl)-1H-indazole-3-carboxylic acid.

Procedure 4

Procedure 4 provides a preparation of substituted benzisothiazole-3-carboxylic acids from the corresponding thiophenols.

To a solution of 3-methoxythiophenol (26.7 mmol) in ether (20 mL) was added oxalyl chloride (43 mmol) dropwise. The mixture was heated at reflux for 1.5 h, cooled to rt, and concentrated in vacuo. The resulting yellow oil was dissolved in dichloromethane (50 mL), cooled to 0° C., and was treated with aluminum chloride (32.0 mmol) in portions. The mixture was heated at reflux for 30 min, cooled to rt, and poured onto ice water with stirring. The organic layer was separated and successively washed with saturated, aqueous sodium bicarbonate, water, and brine. The organic layer was dried over magnesium sulfate, filtered and concentrated in vacuo. The residue was purified by chromatography (4/1 ethyl acetate/hexane) which provided 6-methoxy-1-benzothiophene-2,3-dione (47%) as an orange solid.

To a mixture of the dione (0.44 mmol) in 30% aqueous solution of ammonium hydroxide (2.0 mL) was added 35% aqueous solution hydrogen peroxide (0.2 mL) and the reaction mixture was maintained for 12 h. The precipitated pink solids were isolated by filtration, washed with water, and dried under high vacuum to afford 6-methoxybenzisothiazole-3-carboxamide (42%).

To a solution of the amide (5.46 mmol) in methanol (100 mL) was added 10 N sodium hydroxide (12 mL). The mixture was heated at reflux for 12 h, cooled to rt, and was acidified to pH<2 by the slow addition of conc. hydrochloric acid. The organic layer was extracted with dichloromethane (2×) and was dried over sodium sulfate. The crude product was purified by chromatography (300/50/1 dichloromethane/methanol/formic acid) to provide 6-methoxy-1,2-benzisothiazole-3-carboxylic acid (89%) as a pink solid.

The following acids were prepared by this method:
6-Methoxy-1,2-benzisothiazole-3-carboxylic acid, and
6-Ethoxy-1,2-benzisothiazole-3-carboxylic acid.

Procedure 5

Procedure 5 provides a method for the trapping of indazole aryllithiums with ketones and the coupling with 3-aminoquinuclidine to form heterocyclic derivatives.

tert-Butyl 6-bromoindazole-3-carboxylate was prepared from the acid by reaction with a 2-fold excess of di-tert-butyldicarbonate followed by treatment with sodium hydroxide. To a suspension of sodium hydride (60% mineral oil dispersion) (4.8 mmol) in tetrahydrofuran (40 mL) at 0° C. was slowly added a solution of tert-butyl 6-bromoindazole-3-carboxylate (4.0 mmol) in tetrahydrofuran (4 mL). After stirring for 0.5 h at 0° C., the mixture was cooled to −78° C. and a 1.7 M solution of tert-butyllithium in pentane (5.1 mmol) was added. After 0.5 h at −78° C., a solution of tetrahydropyran-4-one (5 mmol) in tetrahydrofuran (1 mL) was added dropwise. The mixture was stirred at −78° C. for 1 h and warmed to 0° C. The reaction mixture was quenched with saturated aqueous ammonium chloride and the mixture was partitioned between ethyl acetate (100 mL) and water (100 mL). The organic layer was separated, washed with brine (50 mL), dried (magnesium sulfate), and concentrated. The residue was purified by chromatography (70/30 ethyl acetate/hexanes) to yield 6-(4-hydroxytetrahydropyran-4-yl)-1H-indazole-3-carboxylic acid tert-butyl ester (68%) as a colorless solid.

6-(4-Hydroxytetrahydropyran-4-yl)-1H-indazole-3-carboxylic acid tert-butyl ester (0.86 mmol) was dissolved in trifluoroacetic acid (3 mL) and the mixture was maintained at room temperature for 16 h. The solvent was removed in vacuo and the residue was triturated with ethyl acetate to provide 6-(3,6-dihydro-2H-pyran-4-yl)-1H-indazole-3-carboxylic acid (76%).

6-(4-Hydroxytetrahydropyran-4-yl)-1H-indazole-3-carboxylic acid tert-butyl ester (1.0 mmol) was dissolved in trifluoroacetic acid (5 mL), triethylsilane (2 mL), and dichloromethane (3 mL) and the mixture was refluxed for 16 h. The solvent was removed in vacuo and the residue was triturated with ethyl acetate to provide 6-(tetrahydropyran-4-yl)-1H-indazole-3-carboxylic acid (60%) as a tan solid.

The following acids were prepared using this method:
5-(3,6-Dihydro-2H-pyran-4-yl)-1H-indazole-3-carboxylic acid,
6-(3,6-Dihydro-2H-pyran-4-yl)-1H-indazole-3-carboxylic acid,
5-(Tetrahydro-2H-pyran-4-yl)-1H-indazole-3-carboxylic acid, and
6-(Tetrahydro-2H-pyran-4-yl)-1H-indazole-3-carboxylic acid.

Procedure 6

Procedure 6 provides a method for the preparation of 6-difluoromethoxyindazole-3-acid from 4-nitrophenol.

4-Nitrophenol (162 mmol) was added to a suspension of sodium hydroxide (485 mmol) in N,N-dimethylformamide (150 mL) and the suspension was maintained for 15 min at rt. The reaction mixture was cooled to 0° C. and was treated with ethyl chlorodifluoroacetate (329 mmol). The reaction mixture was heated at 70° C. for 16 h and was concentrated. The residue was diluted with ice water (200 mL) and was extracted with ethyl acetate (3×100 mL). The combined organic layers were dried (magnesium sulfate) and concentrated to provide the difluoromethyl ether in 59% yield as a yellow oil.

The nitro ether (149 mmol) was dissolved in ethanol (37.5 mL), diluted with water (25 mL), and was treated with ammonium chloride (84.7 mmol) and iron powder (105 mmol). The reaction mixture was heated at reflux for 30 minutes and the suspension was filtered through Celite. The filter cake was washed with ethanol three times and the combined filtrates were concentrated. The residue was dissolved in water and the pH adjusted to 9-10 with 5 M sodium hydroxide. The aqueous layer was extracted with ethyl acetate (3×100 mL) and the combined organic layers were dried (magnesium sulfate) and concentrated to a yellow oil. The oil was dissolved in acetic anhydride (23.5 mmol) and the reaction mixture was maintained at rt for 16 h. The reaction mixture was diluted with water (50 mL) and was neutralized with solid sodium bicarbonate. The precipitated solids were isolated by filtration, washed with water, and dried to provide the acetamide in 62% yield as a light yellow solid.

Acetic anhydride (19.6 mmol) was added to a solution of the acetamide (13.2 mmol) in chloroform (20 μL) and the reaction mixture was warmed to reflux. Fuming nitric acid (16.0 mmol) was added dropwise and the reaction mixture was maintained at reflux for 30 min. The cooled solution was diluted with water (20 mL) and the aqueous layer was extracted with dichloromethane (3×100 mL). The combined organic layers were dried (magnesium sulfate) and concentrated to provide the nitro-amide in 83% yield.

The amide (11.0 mmol), sodium hydroxide (43.8 mmol), and water (10 mL) were combined and the reaction mixture was maintained for 1.5 hour at 60° C. The reaction was allowed to cool to rt and the precipitated solids were isolated by filtration, and washed with water, and dried to provide the aniline in 98% yield as a light yellow solid.

The aniline (15.7 mmol) was mixed with 40% hydrobromic acid (14.3 g) and water (10 mL) and the reaction mixture was warmed to 80-90° C. in order to completely dissolve the aniline. The reaction mixture was cooled to 0° C. and a solution of sodium nitrite (23.2 mmol) in water (5.3 mL) was added during a 15 min period. The solution was maintained for 40 minutes at 0-5° C. and filtered. Copper (I) bromide (18.8 mmol) was dissolved in 40% hydrobromic acid (21 mL) and was cooled to 0° C. The solution of the diazo salt was added slowly to the copper solution and the mixture was maintained for 30 min at 0-10° C. The reaction mixture was heated at 60° C. for 30 min and then at 100° C. for 10 min to ensure completion. The reaction mixture was allowed to cool to rt and was extracted with dichloromethane (3×40 mL). The combined organic layers were washed with 1 M sodium hydroxide, water, 1 N hydrochloric acid, and water. The organic layer was dried (magnesium sulfate) and concentrated to provide the nitro bromide in 76% yield as a light yellow solid.

Diethyl malonate (25.7 mmol) was added dropwise to a suspension of sodium hydride (25.8 mmol) in dimethylsulfoxide (5 mL) at 0° C. The reaction mixture was warmed to 60° C. and maintained for 30 min. A solution of the nitro bromide (11.7 mmol) in dimethylsulfoxide (71 mL) was added dropwise and the reaction mixture was heated at 100° C. for 5 h. The cooled solution was poured onto ice water and the aqueous layer was extracted with dichloromethane (3×100 mL). The combined organic layers were dried (magnesium sulfate) and concentrated to give the crude diester as an oil. The diester (11.7 mmol), sodium hydroxide (35 mmol), and water (20 mL) were combined and heated at 60° C. for 1 h. The reaction mixture was allowed to cool to rt and the aqueous layer was washed with dichloromethane (3×100 mL). The pH of the aqueous layer was cautiously adjusted to 1 with concentrated hydrochloric acid and the reaction mixture was heated at 60° C. for 1 h. The suspension was cooled to 0° C. and the solids were collected by filtration and dried to provide the acid in 64% yield.

Acetyl chloride (15.3 mmol) was added dropwise to ethanol (50 mL) at 0° C. After 30 min, the acid (7.69 mmol) was added and the reaction mixture was heated at reflux for 15 h. The reaction mixture was concentrated and the residue was partitioned between dichloromethane (20 mL) and saturated sodium bicarbonate (10 mL). The aqueous layer was further extracted with dichloromethane (2×20 mL) and the combined organic layers were dried (magnesium sulfate) and concentrated to provide the ester in 94% yield as a brown oil.

Acetic anhydride (6.0 mL) was added to a suspension of the ester (3.64 mmol), and acetic acid (7.0 mL) at 0° C. Zinc dust (14.6 mmol) was added in portions over 15 min and the reaction mixture was maintained for 30 min at 0° C. and then for 1.5 h at rt. Additional zinc powder (6.15 mmol) was added and the reaction maintained for 3 h. The suspension was filtered through Celite and the filtrate was concentrated. The residue was partitioned between saturated sodium bicarbonate (10 mL) and ethyl acetate (20 mL). The aqueous layer was further extracted with ethyl acetate (3×20 mL) and the combined organic layers were dried (magnesium sulfate) and concentrated to provide the acetamide in 92% yield as a brown oil.

Acetic anhydride (13.7 mmol), isoamyl nitrite (13.7 mmol), and potassium acetate (2.04 mmol) were added to a solution of the acetamide (3.92 mmol) in chloroform (20 mL)

and the suspension was heated at reflux for 16 h. The solution was evaporated and the residue was partitioned between saturated sodium bicarbonate (10 µL) and dichloromethane (20 mL). The aqueous layer was further extracted with dichloromethane (2×20 mL) and the combined organic layers were dried (magnesium sulfate) and concentrated to provide the crude N-acetylindazole ester as a brown oil.

The ester (3.36 mmol), sodium hydroxide (10 mmol) and water (5 mL) were combined and the reaction was maintained for 24 h at 60° C. After cooling to rt, the aqueous layer was washed with dichloromethane (3×30 mL). The aqueous layer was adjusted to pH 1 with concentrated hydrochloric acid and the precipitated solids were collected by filtration, washed with water and dichloromethane, and dried to provide the acid in 26% yield.

The following acid was prepared according to this method: 6-(Difluoromethoxy)-1H-indazole-3-carboxylic acid.

II. Base Synthesis

Procedure 7

Procedure 6 details the preparation of 3-aminomethylquinuclidine from quinuclidinone.

A solution of tosylmethylisocyanide (50.0 mmol) in ethanol (4 mL) was added to the solution of quinuclidone (40.0 mmol) in ethylene glycol dimethyl ether (155 mL) and the mixture was cooled to −5° C. Solid potassium tert-butoxide (130 mmol) was added in portions over 20 minutes. The reaction mixture was allowed to warm to RT after 30 min and was maintained for an additional 3 hours. The reaction mixture was filtered and diluted with saturated hydrochloric acid in isopropanol. Diethyl ether was added and the solids were collected by filtration to provide the desired product in 88% yield as a yellow solid.

Concentrated hydrochloric acid (12 mL) and 10% palladium on carbon (9.6 g) were added to a solution of the nitrile (35.0 mmol) in methanol (720 mL) at 0° C. The reaction mixture was maintained under an atmosphere of hydrogen gas for 4.5 hours. The catalyst was removed by filtration through Celite and the filtrate was concentrated to afford a yellow solid. This solid was dissolved in methanol and re-precipitated with ethyl ether (400 mL). The solids were collected by filtration and dried to provide the desired product in 32% yield as a yellow solid. $^1$H NMR (CD$_3$OD) δ 3.30 (m, 1 H), 3.14 (m, 4 H), 2.90 (m, 2 H), 2.85 (m, 1 H), 2.2 (m1 H), 2.0 (m, 1 H), 1.85 (m, 2 H), 1.6 (m, 1 H).

III. Coupling and Derivatization Procedures

Representative Procedure A.
Procedure A provides a method for ester formation using Mitsunobu conditions.

Example 1

(3S)-1-Azabicyclo[2.2.2]oct-3-yl 6-(5-methyl-1,3-thiazol-2-yl)-1H-indazole-3-carboxylate hydroformate

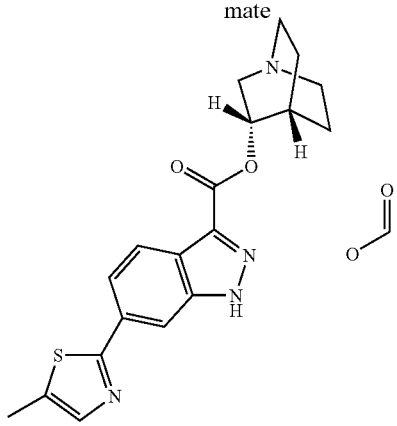

To a solution of 6-(5-methyl-1,3-thiazol-2-yl)-1H-indazole-3-carboxylic acid (0.50 mmol), (3R)-quinuclidin-3-ol (0.57 mmol), and triphenylphosphine (0.57 mmol) in tetrahydrofuran (5 mL) at 0° C. was added a solution of diisopropyl azodicarboxylate (0.57 mmol) in tetrahydrofuran (1 mL). The mixture was allowed to warm to rt over 2 hours and was maintained for 16 h. The mixture was loaded on a SCX column (5 g) and was washed with methanol. Product was eluted with methanol/dimethylethylamine (9/1) and concentrated. The residue was purified by preparative HPLC to produce the desired product in 1% yield. $^1$H NMR (CD$_3$OD) δ 8.65 (s, 1 H), 8.51 (s, 1 H), 8.04 (d, J=6.0, 1H), 7.74 (d, J=6.0, 1 H), 7.55 (s, 1 H), 5.45 (m, 1 H), 3.81 (m, 1 H), 3.45-3.20 (m, 5H), 2.55 (s, 3 H), 2.55 (m, 1 H), 2.36 (m, 1 H), 2.21-1.93 (m, 3 H); LC/MS (EI) $t_R$ 4.7 min, m/z 369 (M$^+$+1).

Example 2

(3S)-1-Azabicyclo[2.2.2]oct-3-yl 5-(trifluoromethoxy)-1H-indazole-3-carboxylate hydroformate

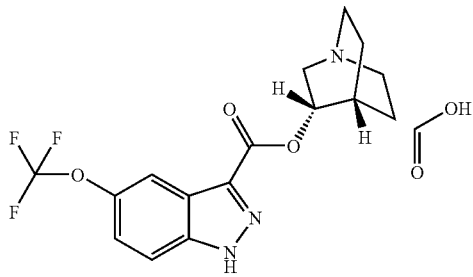

Prepared by Procedure A in 20% yield. LC/MS (EI) $t_R$ 4.8 min, m/z 356 (M$^+$+1).

Example 3

(3S)-1-Azabicyclo[2.2.2]oct-3-yl 6-methoxy-1H-indazole-3-carboxylate hydroformate

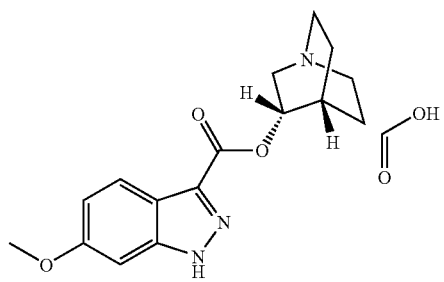

Prepared by Procedure A in 17% yield. LC/MS (EI) $t_R$ 2.4 min, m/z 302 (M$^+$+1).

Example 4

(3S)-1-Azabicyclo[2.2.2]oct-3-yl 5-methoxy-1H-indazole-3-carboxylate hydroformate

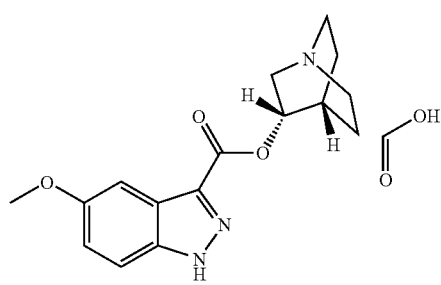

Prepared by Procedure A in 20% yield. LC/MS (E1) $t_R$ 3.3 min, m/z 302 (M$^+$+1).

Example 5

(3S)-1-Azabicyclo[2.2.2]oct-3-yl 6-(trifluoromethoxy)-1H-indazole-3-carboxylate hydroformate

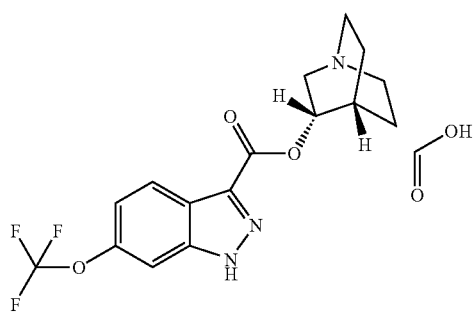

Prepared by Procedure A in 14% yield. LC/MS (EI) $t_R$ 5.0 min, m/z 356 (M$^+$+1).

Example 6

(3S)-1-Azabicyclo[2.2.2]oct-3-yl 5-(difluoromethoxy)-1H-indazole-3-carboxylate hydroformate

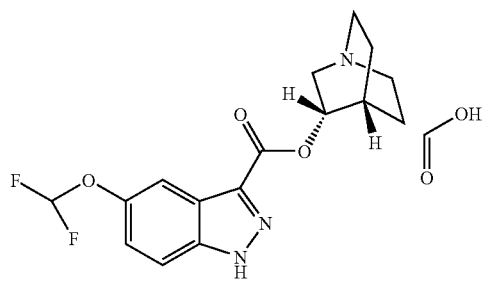

Prepared by Procedure A in 10% yield. LC/MS (EI) $t_R$ 4.3 min, m/z 338 (M$^+$+1).

Example 7

(3S)-1-Azabicyclo[2.2.2]oct-3-yl 5-(5-methyl-1,3-thiazol-2-yl)-1H-indazole-3-carboxylate hydroformate

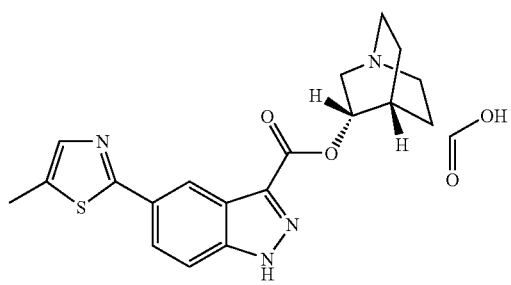

Prepared by Procedure A in 10% yield. LC/MS (EI) $t_R$ 4.7 min, m/z 369 (M$^+$+1).

Example 8

(3S)-1-Azabicyclo[2.2.2]oct-3-yl 5-(4-methyl-1,3-thiazol-2-yl)-1H-indazole-3-carboxylate hydroformate

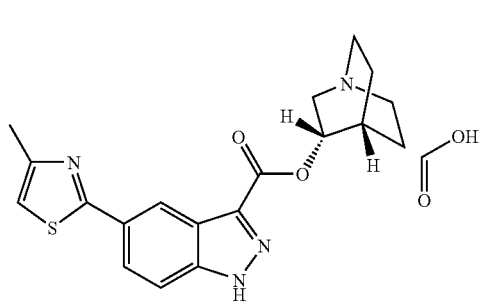

Prepared by Procedure A in 1% yield. LC/MS (EI) $t_R$ 4.7 min, m/z 369 (M$^+$+1).

Example 9

(3S)-1-Azabicyclo[2.2.2]oct-3-yl 5-(tetrahydro-2H-pyran-4-yl)-1H-indazole-3-carboxylate hydroformate

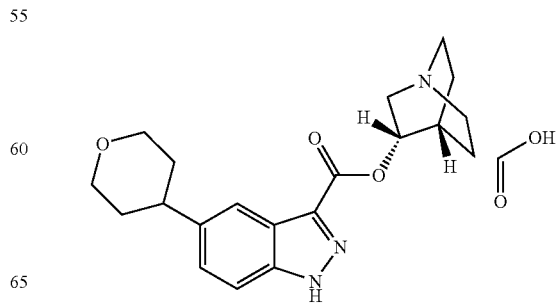

Prepared by Procedure A in 10% yield. LC/MS (EI) $t_R$ 2.8 min, m/z 356 (M$^+$+1).

Example 10

(3S)-1-Azabicyclo[2.2.2]oct-3-yl 6-(3,6-dihydro-2H-pyran-4-yl)-1H-indazole-3-carboxylate hydroformate

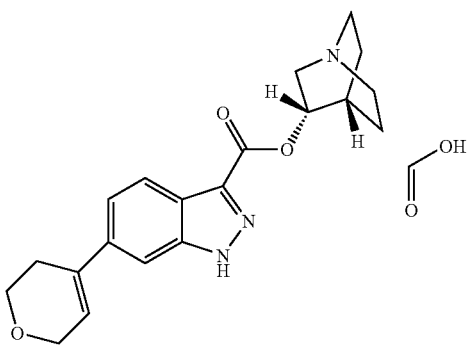

Prepared by Procedure A in 7% yield. LC/MS (EI) $t_R$ 4.3 min, m/z 354 (M$^+$+1).

Example 11

(3S)-1-Azabicyclo[2.2.2]oct-3-yl 6-(tetrahydro-2H-pyran-4-yl)-1H-indazole-3-carboxylate hydroformate

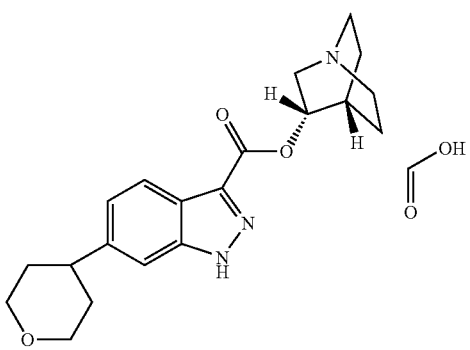

Prepared by Procedure A in 8% yield. LC/MS (EI) $t_R$ 3.0 min, m/z 356 (M$^+$+1).

Representative Procedure B.

Procedure B provides a method for ester formation using tosyl chloride (or oxalyl chloride) activation.

Example 12

(3S)-1-Azabicyclo[2.2.2]oct-3-yl 6-(trifluoromethoxy)-1H-indazole-3-carboxylate

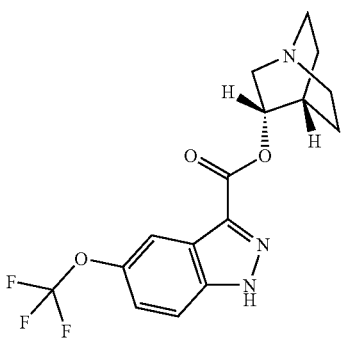

p-Toluenesulfonyl chloride (0.16 mmol) was added to a 0° C. solution of 6-(trifluoromethoxy)-1H-indazole-3-carboxylic acid (0.81 mmol) in pyridine. (5.00 mL). (3S)-Quinuclidin-3-ol (0.81 mmol) was added and the reaction mixture was allowed to warm to rt. The reaction mixture was maintained for 16 h and was filtered and concentrated. The residue was redissolved in methanol and loaded on a 5 g SCX column. The column was washed with methanol and the product was eluted with methanol/dimethylethylamine (9/1) and concentrated. The residue was purified by preparative HPLC to produce the desired product in 16% yield. Note: this procedure works equally well when p-toluenesulfonyl chloride is replaced with oxalyl chloride. $^1$H NMR (CDCl$_3$) δ 8.52 (s, 1 H), 7.96 (d, J=8.9, 1H), 7.49 (s, 1 H), 7.09 (d, J=8.9, 1H), 5.31 (m, 1 H), 3.72-3.29 (m, 6 H), 2.56 (m, 1 H), 2.32 (m, 1 H), 2.06-1.88 (m, 3 H); LC/MS (EI) $t_R$ 4.9 min, m/z 356 (M$^+$+1).

Example 13

(3S)-1-Azabicyclo[2.2.2]oct-3-yl 5-(trifluoromethoxy)-1H-indazole-3-carboxylate

Prepared by Procedure B in 3% yield. LC/MS (EI) $t_R$ 4.8 min, m/z 356 (M$^+$+1).

Example 14

(3S)-1-Azabicyclo[2.2.2]oct-3-yl 6-methoxy-1H-indazole-3-carboxylate

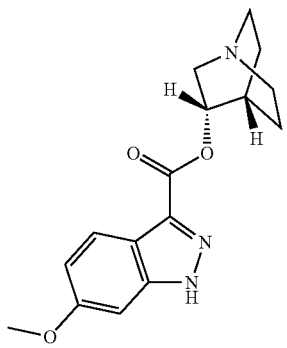

Prepared by Procedure B in 1% yield. LC/MS (EI) $t_R$ 2.5 min, m/z 302 (M$^+$+1).

Example 15

(3S)-1-Azabicyclo[2.2.2]oct-3-yl 5-methoxy-1H-indazole-3-carboxylate

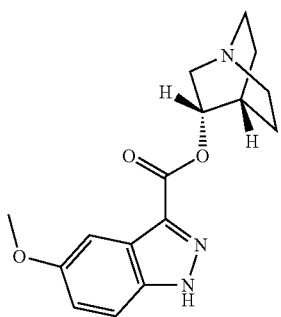

Prepared by Procedure B in 2% yield. LC/MS (EI) $t_R$ 2.5 min, m/z 302 (M$^+$+1).

Example 16

(3S)-1-Azabicyclo[2.2.2]oct-3-yl 5-(1,3-thiazol-2-yl)-1H-indazole-3-carboxylate

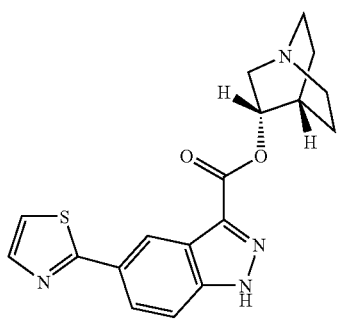

Prepared by Procedure B in 3% yield. LC/MS (EI) $t_R$ 3.9 min, m/z 355 (M$^+$+1).

Example 17

(3S)-1-Azabicyclo[2.2.2]oct-3-yl 5-(5-methyl-1,3-thiazol-2-yl)-1H-indazole-3-carboxylate 4-methyl-benzenesulfonate

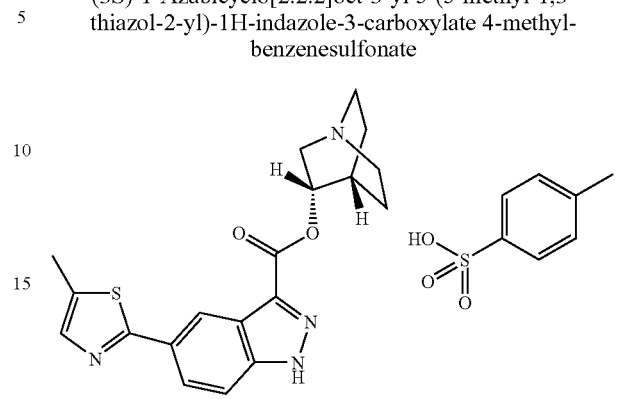

Prepared by Procedure B in 4% yield. LC/MS (EI) $t_R$ 4.8 min, m/z 369 (M$^+$+1).

Example 18

(3S)-1-Azabicyclo[2.2.2]oct-3-yl 5-(4-methyl-1,3-thiazol-2-yl)-1H-indazole-3-carboxylate 4-methyl-benzenesulfonate

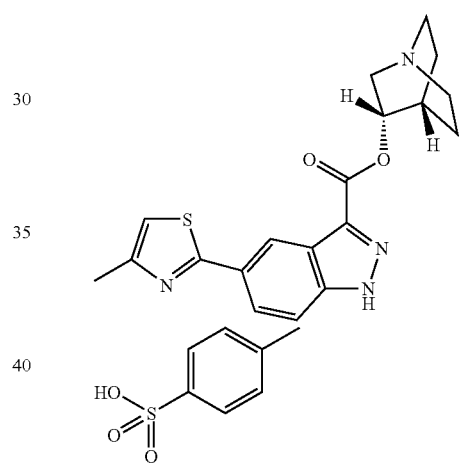

Prepared by Procedure B in 4% yield. LC/MS (EI) $t_R$ 4.8 min, m/z 369 (M$^+$+1).

Example 19

(3S)-1-Azabicyclo[2.2.2]oct-3-yl 6-(5-methyl-1,3-thiazol-2-yl)-1H-indazole-3-carboxylate 4-methyl-benzenesulfonate

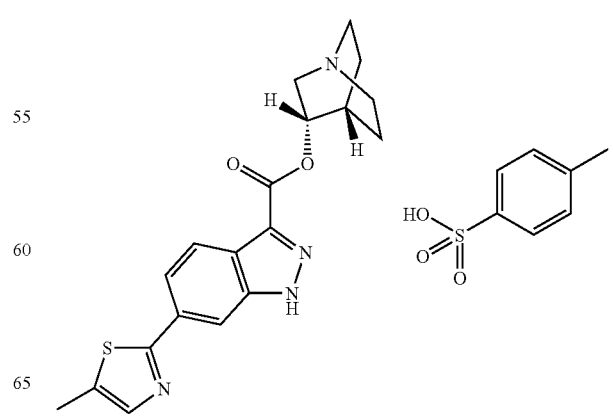

Prepared by Procedure B in 2% yield. LC/MS (EI) $t_R$ 4.8 min, m/z 369 (M$^+$+1).

Example 20

(3S)-1-Azabicyclo[2.2.2]oct-3-yl 6-(4-methyl-1,3-thiazol-2-yl)-1H-indazole-3-carboxylate 4-methyl-benzenesulfonate

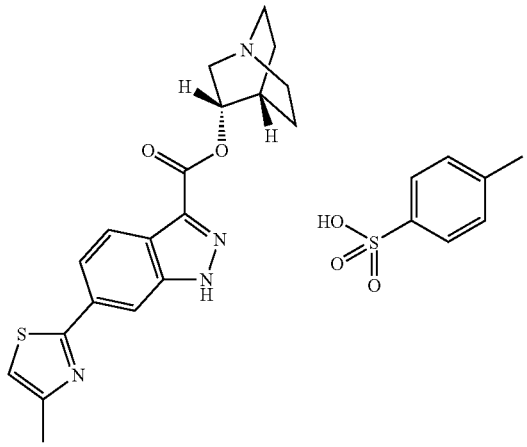

Prepared by Procedure B in 0.3% yield. LC/MS (EI) $t_R$ 4.8 min, m/z 369 (M$^+$+1).

Example 21

(3S)-1-Azabicyclo[2.2.2]oct-3-yl 6-methoxy-1,2-benzisothiazole-3-carboxylate

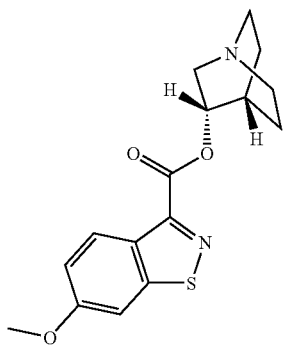

Prepared by Procedure B in 24% yield. LC/MS (EI) $t_R$ 4.3 min, m/z 319 (M$^+$+1).

Example 22

1-azabicyclo[2.2.2]oct-3-yl 5-methoxy-1H-indazole-3-carboxylate hydroformate

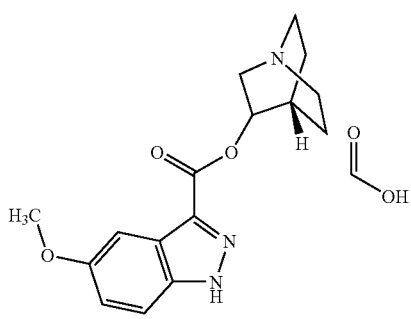

Prepared by Procedure B in 8% yield. LC/MS (EI) $t_R$ 2.9 min, m/z 302 (M$^+$+1).

Example 23

(3S)-1-azabicyclo[2.2.2]oct-3-yl 6-ethoxy-1,2-benzisothiazole-3-carboxylate hydroformate

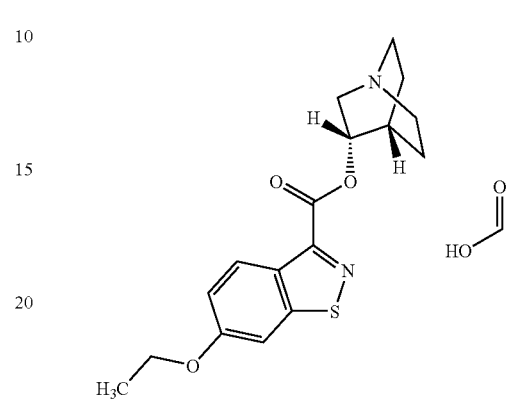

Prepared by Procedure B in 38% yield. LC/MS (EI) $t_R$ 4.7 min, m/z 333 (M$^+$+1).

Example 24

(3R)-1-azabicyclo[2.2.2]oct-3-yl 5-methoxy-1H-indazole-3-carboxylate hydroformate

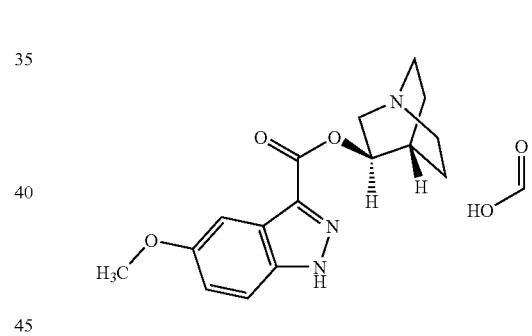

Prepared by Procedure B in 11% yield. LC/MS (EI) $t_R$ 2.5 min, m/z 302 (M++1).

Example 25

((3R)-1-azabicyclo[2.2.2]oct-3-yl 6-methoxy-1H-indazole-3-carboxylate hydroformate

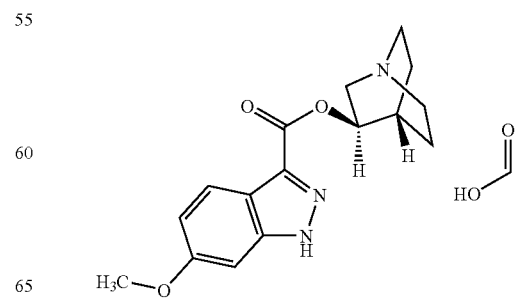

Prepared by Procedure B in 2% yield. LC/MS (EI) $t_R$ 3.3 min, m/z 302 (M$^+$+1).

Example 26

((3R)-1-azabicyclo[2.2.2]oct-3-yl 7-methoxy-1H-indazole-3-carboxylate hydroformate

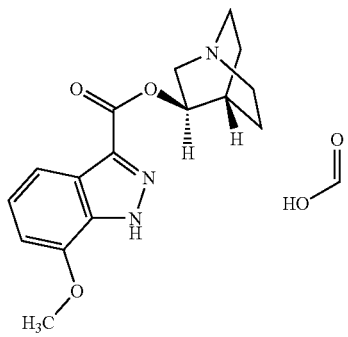

Prepared by Procedure B in 9% yield. LC/MS (EI) $t_R$ 2.9 min, m/z 302 (M$^+$+1).

Example 27

(3R)-1-azabicyclo[2.2.2]oct-3-yl 6-(difluoromethoxy)-1H-indazole-3-carboxylate hydroformate

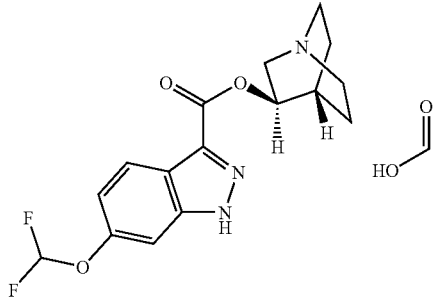

Prepared by Procedure B in 3% yield. LC/MS (EI) $t_R$ 4.7 min, m/z 338 (M$^+$+1).

Example 28

(3R)-1-azabicyclo[2.2.2]oct-3-yl 5-(trifluoromethoxy)-1H-indazole-3-carboxylate

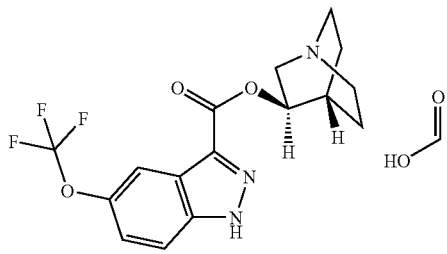

Prepared by Procedure B in 3% yield. LC/MS (EI) $t_R$ 4.9 min, m/z 356 (M$^+$+1).

Example 29

((3R)-1-azabicyclo[2.2.2]oct-3-yl 6-(trifluoromethoxy)-1H-indazole-3-carboxylate hydroformate

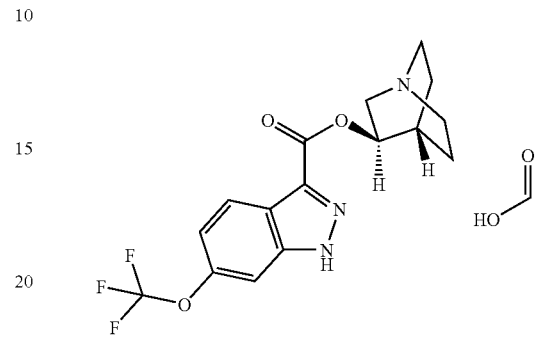

Prepared by Procedure B in 12% yield. LC/MS (EI) $t_R$ 4.9 min, m/z 356 (M$^+$+1).

Example 30

(3R)-1-azabicyclo[2.2.2]oct-3-yl 7-(trifluoromethoxy)-1H-indazole-3-carboxylate hydroformate

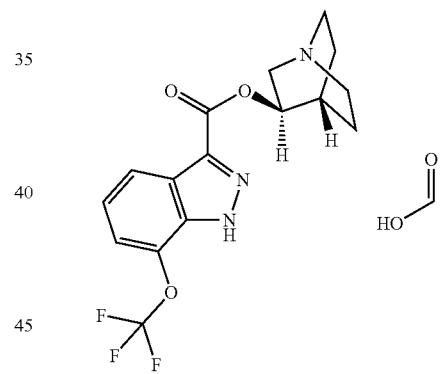

Prepared by Procedure B in 3% yield. LC/MS (EI) $t_R$ 4.8 min, m/z 356 (M$^+$+1).

Example 31

(3R)-1-azabicyclo[2.2.2]oct-3-yl 5-(4-methyl-1,3-thiazol-2-yl)-1H-indazole-3-carboxylate hydroformate

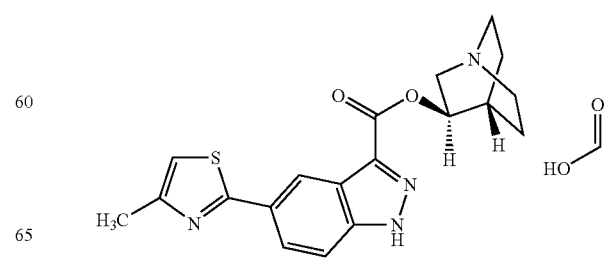

Prepared by Procedure B in 2% yield. LC/MS (EI) $t_R$ 4.8 min, m/z 369 (M$^+$+1).

Example 32

(3R)-1-azabicyclo[2.2.2]oct-3-yl 5-(5-methyl-1,3-thiazol-2-yl)-1H-indazole-3-carboxylate hydroformate

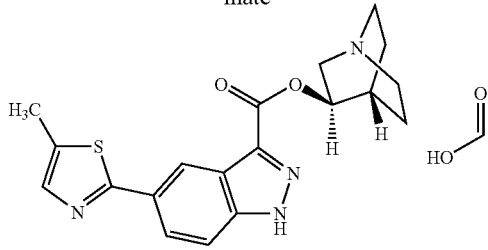

Prepared by Procedure B in 2% yield. LC/MS (EI) $t_R$ 4.8 min, m/z 369 (M$^+$+1).

Example 33

(3R)-1-azabicyclo[2.2.2]oct-3-yl 6-(4-methyl-1,3-thiazol-2-yl)-1H-indazole-3-carboxylate hydroformate

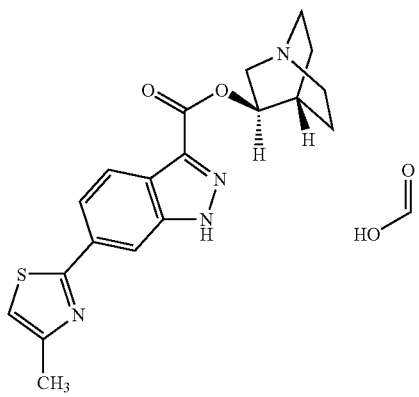

Prepared by Procedure B in 10% yield. LC/MS (EI) $t_R$ 4.8 min, m/z 369 (M$^+$+1).

Example 34

(3R)-1-azabicyclo[2.2.2]oct-3-yl 6-(5-methyl-1,3-thiazol-2-yl)-1H-indazole-3-carboxylate hydroformate

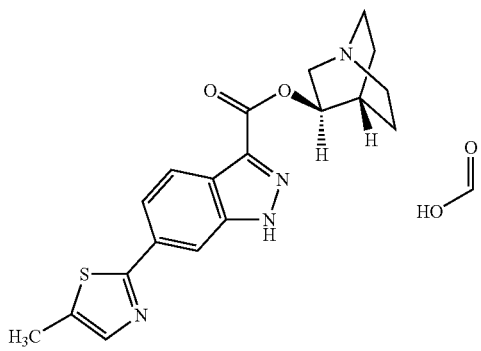

Prepared by Procedure B in 1% yield. LC/MS (EI) $t_R$ 4.9 min, m/z 369 (M$^+$+1).

Example 35

(3R)-1-azabicyclo[2.2.2]oct-3-yl 5-(3,6-dihydro-2H-pyran-4-yl)-1H-indazole-3-carboxylate hydroformate

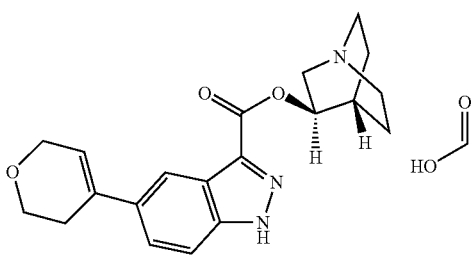

Prepared by Procedure B in 2% yield. LC/MS (EI) $t_R$ 3.9 min, m/z 354 (M$^+$+1).

Representative Procedure C.

Procedure C provides a method for amide formation using HATU activation.

Example 36

N-(1-Azabicyclo[2.2.2]oct-3-ylmethyl)-5-trifluoromethoxy-1H-indazole-3-carboxamide hydroformate

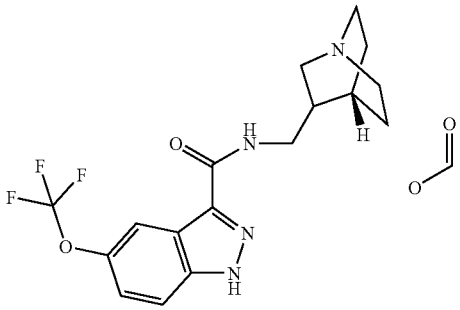

To a solution of 5-(trifluoromethoxy)-1H-indazole-3-carboxylic acid (0.40 mmol) in tetrahydrofuran (5.0 mL) and N,N-dimethylformamide (5.0 mL) was added 1-(1-azabicyclo[2.2.2]oct-3-yl)methanamine dihydrochloride (0.40 mmol) and HATU (0.40 mmol). N,N-Diisopropylethylamine (10.0 mmol) was added and the reaction mixture was maintained for 16 h. The reaction mixture was heated at 60° C. for 1 h, and was filtered and concentrated. The residue was redissolved in methanol and loaded on a 5 g SCX column. The column was washed with methanol and the product was eluted with methanoudimethylethylamine (9/1) and concentrated. The residue was purified by preparative HPLC to produce the desired product in 20% yield. $^1$H NMR (CDCl$_3$) δ 8.47 (s, 1 H), 8.10 (s, 1 H), 7.67 (d, J=9.1, 1H), 7.36 (d, J=9.1, 1H), 3.63-3.52 (m, 3 H), 3.48-3.23 (m, 4 H), 3.08-3.01 (m, 1

H), 2.66-2.44 (m, 1 H), 2.32-2.22 (m, 1 H), 2.14-2.08 (m, 1 H), 2.06-1.85 (m, 3 H); LC/MS (EI) $t_R$ 4.8 min, m/z 369 (M$^+$+1).

Example 37

N-(1-Azabicyclo[2.2.2]oct-3-ylmethyl)-6-methoxy-1H-indazole-3-carboxamide hydroformate

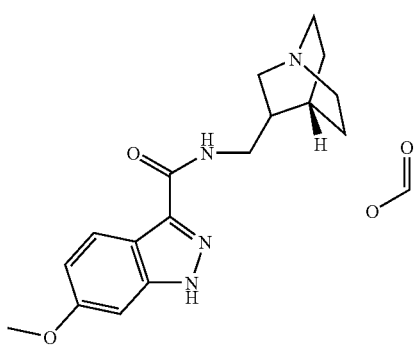

Prepared by Procedure C in 20% yield. LC/MS (EI) $t_R$ 2.5 min, m/z 315 (M$^+$+1).

Example 38

[$^3$H] MLA Binding

Materials:
Rat Brain: Pel-Freez Biologicals, CAT No. 56004-2
Protease inhibitor cocktail tablet: Roche, CAT No. 1697498

Membrane Preparation:
Rat brains in 20 vol (w/v) of ice-cold 0.32 M sucrose with protease inhibitors (one tablet per 50 ml,) were homogenized with a polytron for 10 sec at setting 1 1, then centrifuged 10 min at 1000 g, 4° C. The supernatant was centrifuged again for 20 min at 20,000 g, 4° C. The pellets were resuspended in binding buffer (200 mM TRIS-HCl, 20 mM HEPES, pH 7.5, 144 mM NaCl, 1.5 mM KCl, 1 mM MgSO$_4$, 2 mM CaCl$_2$, 0.1% (w/v) BSA) and stored membrane prep at −80° C.

For saturation assay, the 200 μl assay mixture in binding buffer contains 200 μg of membrane protein, 0.2 to 44 nM of [$^3$H] MLA. The nonspecific binding was defined using 1 μM MLA. Competition assay was carried out with 2 nM [$^3$H] MLA and a desirable range of compounds. The assay mixture was incubated at 22° C. for 2 hours, then harvested with GF/B filter presoaked with 0.3% PEI in binding buffer using Tomtec harvester. The filter was washed three time with binding buffer and the radioactivity was counted with Trilux.

Binding affinities for the preferred compounds of the invention are 1 nM to 10 μM, especially 250 nM to 8 μM.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:
1. A compound according to Formula I:

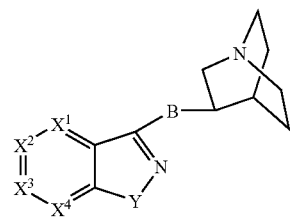

(I)

wherein
$X^1$ to $X^4$ are each, independently, N or CR$^1$, wherein at most one of $X^1$ to $X^4$ is N;
B is —C(O)—O—;
Y is O, S, or NH;
$R^1$ is H,
  C$_{1-4}$-alkyl, or C$_{2-4}$-alkenyl, which, in each case is unsubstituted or substituted one or more times by F, Cl, Br, I, CN, OR$^2$, NR$^3$R$^4$, SH, SR$^3$, SOR$^3$, C$_{3-8}$-cycloalkyl, SO$_2$R$^3$, SO$_2$NR$^3$R$^4$, Ar, Het, or combinations thereof,
  C$_{2-4}$-alkynyl which is unsubstituted or substituted one or more times by F, Cl, Br, I, CN, OR$^2$, NR$^3$R$^4$, SH, SR$^3$, SOR$^3$, C$_{3-8}$-cycloalkyl, SO$_2$R$^3$, SO$_2$NR$^3$R$^4$, Si(C$_{1-6}$-alkyl)$_3$, Ar, Het, or combinations,
  C$_{1-4}$-alkoxy which is unsubstituted or substituted one or more times by F, Cl, Br, I, CN, OR$^2$, NR$^3$R$^4$, SH, SR$^3$, SOR$^3$, C$_{3-8}$-cycloalkyl, SO$_2$R$^3$, SO$_2$NR$^3$R$^4$, Ar, Het, or combinations thereof,
  Ar,
  Het,
  halogen,
  CN, NO$_2$, NR$^3$R$^4$, SR$^4$, SOR$^4$, SO$_2$R$^4$, SO$_2$NR$^3$R$^4$, NR$^3$SO$_2$R$^4$, CONR$^3$R$^4$, CSNR$^3$R$^4$, COOR$^4$, NR$^3$COR$^4$, NR$^3$CSR$^4$, NR$^3$CONR$^3$R$^4$, NR$^3$CSNR$^3$R$^4$, NR$^3$COOR$^4$, NR$^3$CSOR$^4$, OCONR$^3$R$^4$, or OCSNR$^3$R$^4$;
$R^2$ is H,
  C$_{1-6}$-alkyl, C$_{3-8}$-cycloalkyl, or C$_{4-8}$-cycloalkylalkyl, which, in each case, is unsubstituted or substituted one or more by F, Cl, Br, I, CN, OH, alkoxy having 1 to 4 carbon atoms, NR$^3$R$^4$, SH, SR$^3$, SOR$^3$, C$_{3-8}$-cycloalkyl, SO$_2$R$^3$, SO$_2$NR$^3$R$^4$, Ar, Het, or combinations thereof;
$R^3$ and $R^4$ are each independently
  H,
  C$_{1-6}$-alkyl or C$_{3-6}$-alkenyl, which, in each case, is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, C$_{3-8}$-cycloalkyl, Ar, Het, or combinations thereof,
  C$_{3-6}$-alkynyl which is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, C$_{3-8}$-cycloalkyl, Si(C$_{1-6}$-alkyl)$_3$, Ar, Het, or combinations thereof,
  C$_{3-8}$-cycloalkyl which is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, $C_{4-10}$-cycloalkylalkyl which is unsubstituted or substituted in the cycloalkyl portion one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, and/or substituted in the alkyl portion one or more times by one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations, Ar, or Het;

Ar is an aryl group containing 6 to 10 carbon atoms which is unsubstituted or substituted one or more times by
- alkyl having 1 to 8 C carbon atoms,
- alkenyl having 2 to 8 carbon atoms,
- alkynyl having 2 to 8 carbon atoms,
- cycloalkyl having 3 to 8 carbon atoms,
- cycloalkylalkyl having 4 to 10 carbon atoms,
- alkoxy having 1 to 8 carbon atoms,
- halogen,
- amino,
- cyano,
- hydroxyl,
- nitro,
- halogenated alkyl having 1 to 8 carbon atoms,
- halogenated alkoxy having 1 to 8 carbon atoms,
- hydroxyalkyl having 1 to 8 carbon atoms,
- hydroxyalkoxy having 2 to 8 carbon atoms,
- alkenyloxy having 3 to 8 carbon atoms,
- monoalkylamino having 1 to 8 carbon atoms,
- dialkylamino wherein the alkyl portions each have 1 to 8 carbon atoms,
- cycloalkylamino wherein the cycloalkyl portion has 3 to 7 carbon atoms,
- cycloalkylalkylamino wherein the cycloalkylalkyl portion has 4 to 8 carbon atoms,
- carboxy,
- alkoxycarbonyl,
- alkylaminocarbonyl,
- acylamido,
- acyloxy,
- alkylthio having 1 to 8 carbon atoms,
- alkylsulphinyl having 1 to 8 carbon atoms,
- alkylsulphonyl having 1 to 8 carbon atoms,
- sulfo,
- sulfonylamino,
- aryl containing 6 to 10 carbon atoms which is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, cyano, hydroxy, nitro, oxo or thio,
- heterocyclic group which is fully saturated, partially saturated or fully unsaturated, having 5 to 10 ring atoms in which at least 1 ring atom is a N, O or S atom, which is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, cyano, hydroxy, nitro, oxo or thio, or
- combinations thereof; and Het is a heterocyclic group which is fully saturated, partially saturated or fully unsaturated, having 5 to 10 ring atoms in which at least 1 ring atom is a N, O or S atom, which is unsubstituted or substituted one or more times by
- alkyl having 1 to 8 carbon atoms,
- alkenyl having 2 to 8 carbon atoms,
- alkynyl having 2 to 8 carbon atoms,
- cycloalkyl having 3 to 8 carbon atoms,
- cycloalkylalkyl having 4 to 10 carbon atoms,
- alkoxy having 1 to 8 carbon atoms,
- halogen,
- amino,
- cyano,
- hydroxyl,
- nitro,
- halogenated alkyl having 1 to 8 carbon atoms,
- halogenated alkoxy having 1 to 8 carbon atoms,
- hydroxyalkyl having 1 to 8 carbon atoms,
- hydroxyalkoxy having 2 to 8 carbon atoms,
- alkenyloxy having 3 to 8 carbon atoms,
- monoalkylamino having 1 to 8 carbon atoms,
- dialkylamino wherein the alkyl portions each have 1 to 8 carbon atoms,
- cycloalkylamino wherein the cycloalkyl portion has 3 to 7 carbon atoms,
- cycloalkylalkylamino wherein the cycloalkylalkyl portion has 4 to 8 C atoms,
- carboxy,
- alkoxycarbonyl,
- alkylaminocarbonyl,
- acylamido,
- acyloxy,
- alkylthio having 1 to 8 carbon atoms,
- alkylsulphinyl having 1 to 8 carbon atoms,
- alkylsulphonyl having 1 to 8 carbon atoms,
- sulfo,
- sulfonylamino,
- aryl containing 6 to 10 carbon atoms which is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, cyano, hydroxy, nitro, oxo or thio,
- heterocyclic group which is fully saturated, partially saturated or fully unsaturated, having 5 to 10 ring atoms in which at least 1 ring atom is a N, O or S atom, which is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, cyano, hydroxy, nitro, oxo or thio, or combinations thereof; or a pharmaceutically acceptable salt thereof.

2. A compound according to claim 1, wherein $R^1$ is H, $CH_3$, $C_2H_5$, $CF_3$, $C_2H_3$, or $C_3H_5$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, Ar, Het, or combinations thereof, $C_2H$ or $C_3H_3$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, $Si(C_{1-6}\text{-alkyl})_3$, Ar, Het, or combinations thereof, $OCH_3$, $OC_2H_5$, $OCF_3$, or $OCHF_2$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, Ar, Het, or combinations thereof, Ar, Het, F, Cl, Br, I, CN, $NO_2$, $NR^3R^4$, $SR^4$, $SOR^4$, $SO_2R^4$, $SO_2NR^3R^4$, $NR^3SO_2R^4$, $CONR^3R^4$, $CSNR^3R^4$, $COOR^4$, $NR^3COR^4$, $NR^3CSR^4$, $NR^3CONR^3R^4$, $NR^3CSNR^3R^4$, $NR^3COOR^4$, $NR^3CSOR^4$, $OCONR^3R^4$, or $OCSNR^3R^4$;

$R^2$ is H, $CH_3$, $C_2H_5$, $CF_3$, cyclopropyl, cyclobutyl, cyclopentyl, cyclopentylmethyl, or cyclopropylmethyl, which, in each case, is unsubstituted or substituted one or more by F, Cl, Br, I, CN, OH, alkoxy having 1 to 4 carbon atoms, $NR^3R^4$, SH, $SR^3$, $SOR^3$, $C_{3-8}$-cycloalkyl, $SO_2R^3$, $SO_2NR^3R^4$, Ar, Het, or combinations thereof;

$R^3$ and $R^4$ are each independently

H, $CH_3$, $C_2H_5$, $CF_3$, $C_2H_3$, or $C_3H_5$, which, in each case, is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, $C_2H$ or $C_3H_3$, which in each case is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, $Si(C_{1-6}\text{-alkyl})_3$, Ar, Het, or combinations thereof, cyclopropyl, cyclobutyl, or cyclopentyl, which in each case is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, cyclopentylmethyl or cyclopropylmethyl, which in each case is unsubstituted or substituted in the cycloalkyl portion one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, and/or substituted in the alkyl portion one or more times by one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, Ar, or Het;

Ar is phenyl, napthyl or biphenyl, which in each case is unsubstituted or substituted one or more times by halogen, alkyl having 1 to 8 carbon atoms, hydroxy, alkoxy having 1 to 8 carbon atoms, nitro, amino, monoalkylamino having 1 to 8 C atoms, dialkylamino wherein the alkyl portions each have 1 to 8 C atoms, hydroxyalkyl having 1 to 8 carbon atoms, hydroxyalkoxy having 1 to 8 carbon atoms, carboxy, cyano, alkoxycarbonyl 2 to 9 carbon atoms, alkylthio having 1 to 8 carbon atoms, alkylsulphinyl having 1 to 8 C atoms, alkylsulphonyl having 1 to 8 carbon atoms, phenoxy, acetoxy, or combinations thereof; and Het is furyl, thienyl, bithienyl, benzylprazolyl, thiazolyl, imidazolyl, methylimidazolyl, pyrrolidinyl, morpholinyl, thiomorpholinyl, dihydropyranyl, or tetrahydropyranyl, which in each case is unsubstituted or substituted one or more times by halogen, alkyl having 1 to 8 carbon atoms, hydroxy, alkoxy having 1 to 8 carbon atoms, nitro, amino, monoalkylamino having 1 to 8 carbon atoms, dialkylamino wherein the alkyl portions each have 1 to 8 carbon atoms, hydroxyalkyl having 1 to 8 carbon atoms, hydroxyalkoxy having 1 to 8 C atoms, carboxy, cyano, alkoxycarbonyl 2 to 9 carbon atoms, alkylthio having 1 to 8 carbon atoms, alkylsulphinyl having 1 to 8 carbon atoms, alkylsulphonyl having 1 to 8 carbon atoms, phenoxy, acetoxy, or combinations thereof.

3. A compound according to claim 1, wherein said compound is of formula IA:

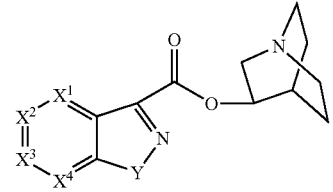

(IA)

and Y is NH or S, or a pharmaceutically acceptable salt thereof.

4. A compound according to claim 1, wherein $X^1$ is CH.

5. A compound according to claim 1, wherein $X^2$ is CH or $CR^1$ in which $R^1$ is Het, $C_{1-4}$-alkoxy, or substituted $C_{1-4}$-alkoxy.

6. A compound according to claim 1, wherein $X^2$ is CH or $CR^1$ in which $R^1$ is thiazolyl, alkyl substituted thiazolyl, tetrahydropyranyl, dihydropyranyl, —$OCH_3$, —$OCF_3$ or $OCHF_2$.

7. A compound according to claim 1, wherein $X^3$ is CH or $CR^1$ in which $R^1$ is Het, $C_{1-4}$-alkoxy, or substituted $C_{1-4}$-alkoxy.

8. A compound according to claim 1, wherein $X^3$ is CH or $CR^1$ in which $R^1$ is thiazolyl, alkyl substituted thiazolyl, tetrahydropyranyl, dihydropyranyl, —$OCH_3$, —$OCF_3$ or $OCHF_2$.

9. A compound according to claim 1, wherein $X^4$ is CH or $CR^1$ in which $R^1$ is substituted or unsubstituted $C_{1-4}$-alkoxy.

10. A compound according to claim 1, wherein $X^4$ is CH or $CR^1$ in which $R^1$ is —$OCF_3$ or $OCHF_2$.

11. A compound according to claim 1, wherein $X^1$ to $X^4$ are each CH or $CR^1$ wherein $R^1$ is not H.

12. A compound according to claim 1, wherein $X^1$ and $X^4$ are each CH.

13. A compound according to claim 1, wherein $X^2$ is $CR^1$ wherein $R^1$ is not H, and $X^1$, $X^3$, and $X^4$ are each CH.

14. A compound according to claim 13, wherein $R^1$ is thiazolyl, alkyl substituted thiazolyl, tetrahydropyranyl, dihydropyranyl, —$OCH_3$, —$OCF_3$ or $OCHF_2$.

15. A compound according to claim 1, wherein $X^3$ is $CR^1$ wherein $R^1$ is not H, and $X^1$, $X^2$, and $X^4$ are each CH.

16. A compound according to claim 15, wherein $R^1$ is thiazolyl, alkyl substituted thiazolyl, tetrahydropyranyl, dihydropyranyl, —$OCH_3$, —$OCF_3$ or $OCHF_2$.

17. A compound according to claim 1, wherein $X^4$ is $CR^1$ wherein $R^1$ is not H, and $X^1$, $X^2$, and $X^3$ are each CH.

18. A compound according to claim 17, wherein $X^4$ is CH or $CR^1$ in which $R^1$ is —$OCF_3$ or $OCHF_2$.

19. A compound according to claim 1, wherein Y is NH or S.

20. A compound according to claim 19, wherein Y is NH.

21. A compound according to claim 1, wherein said compound is selected from:
- (3S)-1-Azabicyclo[2.2.2]oct-3-yl 5-(1,3-thiazol-2-yl)-1H-indazole-3-carboxylate,
- (3S)-1-Azabicyclo[2.2.2]oct-3-yl 5-(4-methyl-1,3-thiazol-2-yl)-1H-indazole-3-carboxylate,
- (3S)-1-Azabicyclo[2.2.2]oct-3-yl 5-(5-methyl-1,3-thiazol-2-yl)-1H-indazole-3-carboxylate,
- (3S)-1-Azabicyclo[2.2.2]oct-3-yl 5-(difluoromethoxy)-1H-indazole-3-carboxylate,
- (3S)-1-Azabicyclo[2.2.2]oct-3-yl 5-(tetrahydro-2H-pyran-4-yl)-1H-indazole-3-carboxylate,
- (3S)-1-Azabicyclo[2.2.2]oct-3-yl 5-(trifluoromethoxy)-1H-indazole-3-carboxylate,
- (3S)-1-Azabicyclo[2.2.2]oct-3-yl 5-methoxy-1H-indazole-3-carboxylate,
- (3S)-1-Azabicyclo[2.2.2]oct-3-yl 6-(3,6-dihydro-2H-pyran-4-yl)-1H-indazole-3-carboxylate,
- (3S)-1-Azabicyclo[2.2.2]oct-3-yl 6-(4-methyl-1,3-thiazol-2-yl)-1H-indazole-3-carboxylate,
- (3S)-1-Azabicyclo[2.2.2]oct-3-yl 6-(5-methyl-1,3-thiazol-2-yl)-1H-indazole-3-carboxylate,
- (3S)-1-Azabicyclo[2.2.2]oct-3-yl 6-(tetrahydro-2H-pyran-4-yl)-1H-indazole-3-carboxylate,
- (3S)-1-Azabicyclo[2.2.2]oct-3-yl 6-(trifluoromethoxy)-1H-indazole-3-carboxylate,
- (3S)-1-Azabicyclo[2.2.2]oct-3-yl 6-methoxy-1,2-benzisothiazole-3-carboxylate,
- (3S)-1-Azabicyclo[2.2.2]oct-3-yl 6-methoxy-1H-indazole-3-carboxylate, and pharmaceutically acceptable salts thereof.

22. A compound according to claim 21, wherein said compound is in the form of a hydroformate salt or the 4-methylbenzenesulfonate salt.

23. A compound according to claim 22, wherein said compound is selected from:
- (3S)-1-Azabicyclo[2.2.2]oct-3-yl 5-(4-methyl-1,3-thiazol-2-yl)-1H-indazole-3-carboxylate 4-methylbenzenesulfonate,
- (3S)-1-Azabicyclo[2.2.2]oct-3-yl 5-(4-methyl-1,3-thiazol-2-yl)-1H-indazole-3-carboxylate hydroformate,
- (3S)-1-Azabicyclo[2.2.2]oct-3-yl 5-(5-methyl-1,3-thiazol-2-yl)-1H-indazole-3-carboxylate 4-methylbenzenesulfonate,
- (3S)-1-Azabicyclo[2.2.2]oct-3-yl 5-(5-methyl-1,3-thiazol-2-yl)-1H-indazole-3-carboxylate hydroformate,
- (3S)-1-Azabicyclo[2.2.2]oct-3-yl 5-(difluoromethoxy)-1H-indazole-3-carboxylate hydroformate,
- (3S)-1-Azabicyclo[2.2.2]oct-3-yl 5-(tetrahydro-2H-pyran-4-yl)-1H-indazole-3-carboxylate hydroformate,
- (3S)-1-Azabicyclo[2.2.2]oct-3-yl 5-(trifluoromethoxy)-1H-indazole-3-carboxylate hydroformate,
- (3S)-1-Azabicyclo[2.2.2]oct-3-yl 5-methoxy-1H-indazole-3-carboxylate hydroformate,
- (3S)-1-Azabicyclo[2.2.2]oct-3-yl 6-(3,6-dihydro-2H-pyran-4-yl)-1H-indazole-3-carboxylate hydroformate,
- (3S)-1-Azabicyclo[2.2.2]oct-3-yl 6-(4-methyl-1,3-thiazol-2-yl)-1H-indazole-3-carboxylate 4-methylbenzenesulfonate,
- (3S)-1-Azabicyclo[2.2.2]oct-3-yl 6-(5-methyl-1,3-thiazol-2-yl)-1H-indazole-3-carboxylate 4-methylbenzenesulfonate,
- (3S)-1-Azabicyclo[2.2.2]oct-3-yl 6-(5-methyl-1,3-thiazol-2-yl)-1H-indazole-3-carboxylate hydroformate,
- (3S)-1-Azabicyclo[2.2.2]oct-3-yl 6-(tetrahydro-2H-pyran-4-yl)-1H-indazole-3-carboxylate hydroformate,
- (3S)-1-Azabicyclo[2.2.2]oct-3-yl 6-(trifluoromethoxy)-1H-indazole-3-carboxylate hydroformate, and
- (3S)-1-Azabicyclo[2.2.2]oct-3-yl 6-methoxy-1H-indazole-3-carboxylate hydroformate.

24. A compound according to claim 1, wherein said compound is selected from:
- 1-Azabicyclo[2.2.2]oct-3-yl 5-methoxy-1H-indazole-3-carboxylate,
- (3S)-1-Azabicyclo[2.2.2]oct-3-yl 6-ethoxy-1,2-benzisothiazole-3-carboxylate,
- (3R)-1-Azabicyclo[2.2.2]oct-3-yl 5-methoxy-1H-indazole-3-carboxylate,
- (3R)-1-Azabicyclo[2.2.2]oct-3-yl 6-methoxy-1H-indazole-3-carboxylate,
- (3R)-1-Azabicyclo[2.2.2]oct-3-yl 7-methoxy-1H-indazole-3-carboxylate,
- (3R)-1-Azabicyclo[2.2.2]oct-3-yl 6-(difluoromethoxy)-1H-indazole-3-carboxylate,
- (3R)-1-Azabicyclo[2.2.2]oct-3-yl 5-(trifluoromethoxy)-1H-indazole-3-carboxylate,
- (3R)-1-Azabicyclo[2.2.2]oct-3-yl 6-(trifluoromethoxy)-1H-indazole-3-carboxylate,
- (3R)-1-Azabicyclo[2.2.2]oct-3-yl 7-(trifluoromethoxy)-1H-indazole-3-carboxylate,
- (3R)-1-Azabicyclo[2.2.2]oct-3-yl 5-(4-methyl-1,3-thiazol-2-yl)-1H-indazole-3-carboxylate,
- (3R)-1-Azabicyclo[2.2.2]oct-3-yl 5-(5-methyl-1,3-thiazol-2-yl)-1H-indazole-3-carboxylate,
- (3R)-1-Azabicyclo[2.2.2]oct-3-yl 6-(4-methyl-1,3-thiazol-2-yl)-1H-indazole-3-carboxylate,
- (3R)-1-Azabicyclo[2.2.2]oct-3-yl 6-(5-methyl-1,3-thiazol-2-yl)-1H-indazole-3-carboxylate,
- (3R)-1-Azabicyclo[2.2.2]oct-3-yl 5-(3,6-dihydro-2H-pyran-4-yl)-1H-indazole-3-carboxylate, and pharmaceutically acceptable salts thereof.

25. A compound according to claim 24, wherein said compound is in the form of a hydroformate salt or the 4-methylbenzenesulfonate salt.

26. A compound according to claim 25, wherein said compound is selected from:
- 1-Azabicyclo[2.2.2]oct-3-yl 5-methoxy-1H-indazole-3-carboxylate hydroformate,
- (3S)-1-Azabicyclo[2.2.2]oct-3-yl 6-ethoxy-1,2-benzisothiazole-3-carboxylate hydroformate,
- (3R)-1-Azabicyclo[2.2.2]oct-3-yl 5-methoxy-1H-indazole-3-carboxylate hydroformate,
- (3R)-1-Azabicyclo[2.2.2]oct-3-yl 6-methoxy-1H-indazole-3-carboxylate hydroformate, (3R)-1-Azabicyclo[2.2.2]oct-3-yl 7-methoxy-1H-indazole-3-carboxylate hydroformate,
(3R)-1-Azabicyclo[2.2.2]oct-3-yl 6-(difluoromethoxy)-1H-indazole-3-carboxylate hydroformate,
(3R)-1-Azabicyclo[2.2.2]oct-3-yl 6-(trifluoromethoxy)-1H-indazole-3-carboxylate hydroformate,
(3R)-1-Azabicyclo[2.2.2]oct-3-yl 7-(trifluoromethoxy)-1H-indazole-3-carboxylate hydroformate,
(3R)-1-Azabicyclo[2.2.2]oct-3-yl 5-(4-methyl-1,3-thiazol-2-yl)-1H-indazole-3-carboxylate hydroformate,
(3R)-1-Azabicyclo[2.2.2]oct-3-yl 5-(5-methyl-1,3-thiazol-2-yl)-1H-indazole-3-carboxylate hydroformate,
(3R)-1-Azabicyclo[2.2.2]oct-3-yl 6-(4-methyl-1,3-thiazol-2-yl)-1H-indazole-3-carboxylate hydroformate,
(3R)-1-Azabicyclo[2.2.2]oct-3-yl 6-(5-methyl-1,3-thiazol-2-yl)-1H-indazole-3-carboxylate hydroformate.

27. A pharmaceutical composition comprising a compound according to claim 1 and a pharmaceutically acceptable carrier.

28. A compound according to claim 1, wherein $X^1$ to $X^4$ are each, independently, $CR^1$.

29. A compound according to claim 28, wherein:
$R^1$ is H,
$CH_3$, $C_2H_5$, $C_2H_3$, or $C_3H_5$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, Ar, Het, or combinations thereof,
$C_2H$ or $C_3H_3$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, $Si(C_{1-6}\text{-alkyl})_3$, Ar, Het, or combinations thereof,
$OCH_3$, or $OC_2H_5$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_2R^3$, $SO_2NR^3R^4$, Ar, Het, or combinations thereof,
Ar,
Het, or
F, Cl, Br, I, CN, $NO_2$, $NR^3R^4$, $SR^4$, $SOR^4$, $SO_2R^4$, $SO_2NR^3R^4$, $NR^3SO_2R^4$, $CONR^3R^4$, $CSNR^3R^4$, $COOR^4$, $NR^3COR^4$, $NR^3CSR^4$, $NR^3CONR^3R^4$, $NR^3CSNR^3R^4$, $NR^3COOR^4$, $NR^3CSOR^4$, $OCONR^3R^4$, or $OCSNR^3R^4$;
$R^2$ is H,
$CH_3$, $C_2H_5$, cyclopropyl, cyclobutyl, cyclopentyl, cyclopentylmethyl, or cyclopropylmethyl, which, in each case, is unsubstituted or substituted one or more by F, Cl, Br, I, CN, OH, alkoxy having 1 to 4 carbon atoms, $NR^3R^4$, SH, $SR^3$, $SOR^3$, $C_{3-8}$-cycloalkyl, $SO_2R^3$, $SO_2NR^3R^4$, Ar, Het, or combinations thereof;
$R^3$ $R^4$ each independently
H,
$CH_3$, $C_2H_5$, $C_2H_3$, or $C_3H_5$, which, in each case, is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof,
$C_2H$ or $C_3H_3$, which in each case is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, $Si(C_{1-6}\text{-alkyl})_3$, Ar, Het, or combinations thereof,
cyclopropyl, cyclobutyl, or cyclopentyl, which in each case is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof,
cyclopentylmethyl or cyclopropylmethyl, which in each case is unsubstituted or substituted in the cycloalkyl portion one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, and/or substituted in the alkyl portion one or more times by one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof,
Ar, or
Het;
Ar is phenyl, naphthyl or biphenyl, which in each case is unsubstituted or substituted one or more times by halogen, alkyl having 1 to 8 carbon atoms, hydroxy, alkoxy having 1 to 8 carbon atoms, nitro, amino, monoalkylamino having 1 to 8 carbon atoms, dialkylamino wherein the alkyl portions each have 1 to 8 carbon atoms, hydroxyalkyl having 1 to 8 carbon atoms, hydroxyalkoxy having 1 to 8 carbon atoms, carboxy, cyano, alkoxycarbonyl 2 to 9 carbon atoms, alkylthio having 1 to 8 carbon atoms, alkylsulphinyl having 1 to 8 carbon atoms, alkylsulphonyl having 1 to 8 carbon atoms, phenoxy, acetoxy, or combinations thereof; and
Het is furyl, thienyl, bithienyl, benzylprazolyl, thiazolyl, imidazolyl, methylimidazolyl, pyrrolidinyl, morpholinyl, thiomorpholinyl, dihydropyranyl, or tetrahydropyranyl, which in each case is unsubstituted or substituted one or more times by halogen, alkyl having 1 to 8 carbon atoms, hydroxy, alkoxy having 1 to 8 carbon atoms, nitro, amino, monoalkylamino having 1 to 8 carbon atoms, dialkylamino wherein the alkyl portions each have 1 to 8 carbon atoms, hydroxyalkyl having 1 to 8 carbon atoms, hydroxyalkoxy having 1 to 8 carbon atoms, carboxy, cyano, alkoxycarbonyl 2 to 9 carbon atoms, alkylthio having 1 to 8 carbon atoms, alkylsulphinyl having 1 to 8 C carbon atoms, alkylsulphonyl having 1 to 8 carbon atoms, phenoxy, acetoxy, or combinations thereof.

30. A compound according to claim 28, wherein
$X^2$ is $CR^1$ wherein $R^1$ is not H, and $X^1$, $X^3$, and $X^4$ are each CH;
$X^3$ is $CR^1$ wherein $R^1$ is not H, and $X^1$, $X^2$, and $X^4$ are each CH;
$X^4$ is $CR^1$ wherein $R^1$ is not H, and $X^1$, $X^2$, and $X^3$ are each CH.

31. A compound according to claim 28, wherein $R^1$ is H or Het.

32. A compound according to claim 29, wherein:

R is H, $CH_3$, $C_2H_5$, $CF_3$, $C_2H_3$, or $C_3H_5$, $C_2H$ or $C_3H_3$, which in each case is unsubstituted or substituted one or more times by F, Cl, Br, I, CN, $OR^2$, $NR^3R^4$, SH, $SR^3$, $SOR^3$, $C_{3-8}$-cycloalkyl, $SO_R^3$, $SO_2NR^3R^4$, $Si(C_{1-6}$-alkyl$)_3$, Ar, Het, or combinations thereof, $OCH_3$, $OC_2H_5$, $OCF_3$, or $OCHF_2$, Ar, Het, or F, Cl, Br, I, CN, $NO_2$, $NR^3R^4$, $SR^4$, $SOR^4$, $SO_2R^4$, $SO_2NR^3R^4$, $NR^3SO_2R^4$, $CONR^3R^4$, $CSNR^3R^4$, $COOR^4$, $NR^3COR^4$, $NR^3CSR^4$, $NR^3CONR^3R^4$, $NR^3CSNR^3R^4$, $NR^3COOR^4$, $NR^3CSOR^4$, $OCONR^3R^4$, or $OCSNR^3R^4$;

$R^2$ is H, or $CH_3$, $C_2H_5$, $CF_3$, cyclopropyl, cyclobutyl, cyclopentyl, cyclopentylmethyl, or cyclopropylmethyl; and $R^3$ $R^4$ are each independently

H, $CH_3$, $C_2H_5$, $CF_3$, $C_2H_3$, or $C_3H_5$, $C_2H$ or $C_3H_3$, which in each case is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, $Si(C_{1-6}$-alkyl$)_3$, Ar, Het, or combinations thereof, cyclopropyl, cyclobutyl, or cyclopentyl, which in each case is unsubstituted or substituted one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, cyclopentylmethyl or cyclopropylmethyl, which in each case is unsubstituted or substituted in the cycloalkyl portion one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, and/or substituted in the alkyl portion one or more times by one or more times by F, Cl, Br, I, CN, alkoxy having 1 to 6 carbon atoms, monoalkylamino having 1 to 6 carbon atoms, dialkylamino wherein each alkyl group has 1 to 6 carbon atoms, $C_{3-8}$-cycloalkyl, Ar, Het, or combinations thereof, Ar, or Het.

33. A compound according to claim 32, wherein $X^2$ is $CR^1$ wherein $R^1$ is not H, and $X^1$, $X^3$, and $X^4$ are each CH;

$X^3$ is $CR^1$ wherein $R^1$ is not H, and $X^1$, $X^2$, and $X^4$ are each CH;

$X^4$ is $CR^1$ wherein $R^1$ is not H, and $X^1$, $X^2$, and $X^3$ are each CH.

34. A compound according to claim 32, wherein $R^1$ is H or Het.

* * * * *

UNITED STATES PATENT AND TRADEMARK OFFICE
CERTIFICATE OF CORRECTION

| | |
|---|---|
| PATENT NO. | : 7,625,924 B2 |
| APPLICATION NO. | : 11/312831 |
| DATED | : December 1, 2009 |
| INVENTOR(S) | : Truc Minh Nguyen |

Page 1 of 1

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (345) days Delete the phrase "by 345 days" and insert -- by 675 days --

Signed and Sealed this

Fourth Day of May, 2010

David J. Kappos
*Director of the United States Patent and Trademark Office*